United States Patent [19]

Ginsberg et al.

[11] Patent Number: 5,492,890
[45] Date of Patent: Feb. 20, 1996

[54] POLYPEPTIDES FOR PROMOTING CELL ATTACHMENT

[75] Inventors: Mark H. Ginsberg; Edward F. Plow, both of San Diego; Ronald Bowditch, Encinitas, all of Calif.

[73] Assignee: The Scripps Research Institute, La Jolla, Calif.

[21] Appl. No.: 804,224

[22] Filed: Dec. 5, 1991

Related U.S. Application Data

[63] Continuation-in-part of Ser. No. 803,623, Nov. 27, 1991, which is a continuation-in-part of Ser. No. 725,600, Jul. 3, 1991, abandoned, which is a continuation-in-part of Ser. No. 620,668, Dec. 3, 1990, abandoned.

[51] Int. Cl.$^6$ .................... A61K 38/36; A61K 35/14; C07K 14/75
[52] U.S. Cl. ................... 514/12; 514/2; 514/21; 530/350; 530/382; 530/324
[58] Field of Search ................... 435/69.1, 69.7, 435/172.1, 240.1, 320.1; 536/27; 514/12, 2, 21; 530/324, 350, 395, 382

[56] References Cited

U.S. PATENT DOCUMENTS

| | | | |
|---|---|---|---|
| 4,578,079 | 3/1986 | Ruoslahti et al. | 623/11 |
| 4,792,525 | 12/1988 | Ruoslahti et al. | 530/324 |
| 4,980,279 | 12/1990 | Peters et al. | 530/395 |
| 5,019,646 | 5/1991 | Furcht et al. | 530/326 |
| 5,049,658 | 9/1991 | Kimizuka et al. | 530/350 |

OTHER PUBLICATIONS

Ruoslahti, E., et al., Methods in Enzymology, vol. 82, pp. 803–831, 1982.
Kornblihtt, A. R., et al., The EMBO Journal, vol. 4, No. 7, pp. 1755–1759, Jul., 1985.
Ginsberg, M., et al., The Journal of Biological Chemistry, vol. 260, No. 7, pp. 3931–3936, Apr., 1985.
Obara et al. (1988, May 20) Cell 53:649–657.
Guan et al. (1988) Gene 67:21–30.
Church et al. (1991, Jun. 25) J. Biol. Chem. 266(18):11975–11979.
Akiyama et al. (1985) J. Biol Chem. 260(19):10402–10405.
Akiyama et al. (1985) J. Biol Chem. 260(24):13256–13260.
Aota et al. (1991, Aug. 25) J. Biol. Chem. 266(24):15938–15943.
Bowditch et al. (1991, Dec. 5) J. Biol. Chem. 266(34):23323–23328.
Frenz et al. (1989) Developmental Biol. 136:87–96.
Garcia–Pardo et al. (1990, May 1) J. Immunology 144(9):3361–3366.
Komoriya et al. (1991, Aug. 15) J. Biol. Chem. 266(23):15075–15079.
McCarthy et al. (1990, Mar.) J. Cell Biol. 110:777–787.
Mould et al. (1990, Mar. 5) J. Biol. Chem. 265(7):4020–4024.
Mould et al. (1991, Feb. 25) J. Biol. Chem. 266(6):3579–3585.
Mould et al. (1991) EMBO J. 10(13):4089–4095.
Nagai et al. (1991, Sep.) J. Cell Biol. 114(6):1295–1305.
Obara et al. (1987, Mar.) FEBS Lett. 213(2):261–264.
Wayner et al. (1989, Sep.) J. Cell. Biol. 109:1321–1330.

Primary Examiner—Robert A. Wax
Assistant Examiner—Keith D. Hendricks
Attorney, Agent, or Firm—Thomas Fitting

[57] ABSTRACT

Novel polypeptides derived from human fibronectin, and fusion proteins containing those peptide sequences are described which define a receptor binding site on fibronectin that binds to the platelet receptor glycoprotein GPIIb-IIIa expressed by cells. The receptor binding site of human fibronectin includes at least fibronectin amino acid residues 1410–1436. The polypeptides facilitate attachment of cells to substrates either alone or in conjunction with RGD-containing peptides. Vectors preparing the fusion proteins and antibodies are also described. Methods for promoting cell attachment and for inhibiting cell adhesion are also described.

4 Claims, 4 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 606 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..606

( x i ) SEQUENCE DESCRIPTION: SEQ ID NO:1:

```
CCA  GCT  GTT  CCT  CCT  CCC  ACT  GAC  CTG  CGA  TTC  ACC  AAC  ATT  GGT  CCA      48
Pro  Ala  Val  Pro  Pro  Pro  Thr  Asp  Leu  Arg  Phe  Thr  Asn  Ile  Gly  Pro
 1              5                        10                       15

GAC  ACC  ATG  CGT  GTC  ACC  TGG  GCT  CCA  CCC  CCA  TCC  ATT  GAT  TTA  ACC      96
Asp  Thr  Met  Arg  Val  Thr  Trp  Ala  Pro  Pro  Pro  Ser  Ile  Asp  Leu  Thr
               20                        25                       30

AAC  TTC  CTG  GTG  CGT  TAC  TCA  CCT  GTG  AAA  AAT  GAG  GAA  GAT  GTT  GCA     144
Asn  Phe  Leu  Val  Arg  Tyr  Ser  Pro  Val  Lys  Asn  Glu  Glu  Asp  Val  Ala
          35                        40                       45

GAG  TTG  TCA  ATT  TCT  CCT  TCA  GAC  AAT  GCA  GTG  GTC  TTA  ACA  AAT  CTC     192
Glu  Leu  Ser  Ile  Ser  Pro  Ser  Asp  Asn  Ala  Val  Val  Leu  Thr  Asn  Leu
     50                        55                       60

CTG  CCT  GGT  ACA  GAA  TAT  GTA  GTG  AGT  GTC  TCC  AGT  GTC  TAC  GAA  CAA     240
Leu  Pro  Gly  Thr  Glu  Tyr  Val  Val  Ser  Val  Ser  Ser  Val  Tyr  Glu  Gln
 65                       70                       75                       80

CAT  GAG  AGC  ACA  CCT  CTT  AGA  GGA  AGA  CAG  AAA  ACA  GGT  CTT  GAT  TCC     288
His  Glu  Ser  Thr  Pro  Leu  Arg  Gly  Arg  Gln  Lys  Thr  Gly  Leu  Asp  Ser
                    85                       90                       95

CCA  ACT  GGC  ATT  GAC  TTT  TCT  GAT  ATT  ACT  GCC  AAC  TCT  TTT  ACT  GTG     336
Pro  Thr  Gly  Ile  Asp  Phe  Ser  Asp  Ile  Thr  Ala  Asn  Ser  Phe  Thr  Val
               100                       105                      110

CAC  TGG  ATT  GCT  CCT  CGA  GCC  ACC  ATC  ACT  GGC  TAC  AGG  ATC  CGC  CAT     384
His  Trp  Ile  Ala  Pro  Arg  Ala  Thr  Ile  Thr  Gly  Tyr  Arg  Ile  Arg  His
          115                       120                      125

CAT  CCC  GAG  CAC  TTC  AGT  GGG  AGA  CCT  CGA  GAA  GAT  CGG  GTG  CCC  CAC     432
His  Pro  Glu  His  Phe  Ser  Gly  Arg  Pro  Arg  Glu  Asp  Arg  Val  Pro  His
     130                      135                      140

TCT  CGG  AAT  TCC  ATC  ACC  CTC  ACC  AAC  CTC  ACT  CCA  GGC  ACA  GAG  TAT     480
Ser  Arg  Asn  Ser  Ile  Thr  Leu  Thr  Asn  Leu  Thr  Pro  Gly  Thr  Glu  Tyr
145                       150                      155                      160

GTG  GTC  AGC  ATC  GTT  GCT  CTT  AAT  GGC  AGA  GAG  GAA  AGT  CCC  TTA  TTG     528
Val  Val  Ser  Ile  Val  Ala  Leu  Asn  Gly  Arg  Glu  Glu  Ser  Pro  Leu  Leu
                    165                      170                      175

ATT  GGC  CAA  CAA  TCA  ACA  GTT  TCT  GAT  GTT  CCC  AGG  GAC  CTG  GAA  GTT     576
Ile  Gly  Gln  Gln  Ser  Thr  Val  Ser  Asp  Val  Pro  Arg  Asp  Leu  Glu  Val
               180                      185                      190

GTT  GCT  GCG  ACC  CCC  ACC  AGC  CTA  CTG  ATC                                    606
Val  Ala  Ala  Thr  Pro  Thr  Ser  Leu  Leu  Ile
          195                      200
```

( 2 ) INFORMATION FOR SEQ ID NO:2:

( i ) SEQUENCE CHARACTERISTICS:
        ( A ) LENGTH: 491 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
        ( A ) NAME/KEY: Region
        ( B ) LOCATION: 1..491
        ( D ) OTHER INFORMATION: /note="Sequence Listing Generated
        Residue Positions 1- 409 correspond to native FN
        from positions 1163-1653."

( x i ) SEQUENCE DESCRIPTION: SEQ ID NO:2:

```
Ser Trp Glu Arg Ser Thr Thr Pro Asp Ile Thr Gly Tyr Arg Ile Thr
 1               5                  10                  15

Thr Thr Pro Thr Asn Gly Gln Gln Gly Asn Ser Leu Glu Glu Val Val
            20                  25                  30

His Ala Asp Gln Ser Ser Cys Thr Phe Asp Asn Leu Ser Pro Gly Leu
        35                  40                  45

Glu Tyr Asn Val Ser Val Tyr Thr Val Lys Asp Asp Lys Glu Ser Val
    50                  55                  60

Pro Ile Ser Asp Thr Ile Ile Pro Ala Val Pro Pro Pro Thr Asp Leu
65                  70                  75                  80

Arg Phe Thr Asn Ile Gly Pro Asp Thr Met Arg Val Thr Trp Ala Pro
                85                  90                  95

Pro Pro Ser Ile Asp Leu Thr Asn Phe Leu Val Arg Tyr Ser Pro Val
               100                 105                 110

Lys Asn Glu Glu Asp Val Ala Glu Leu Ser Ile Ser Pro Ser Asp Asn
           115                 120                 125

Ala Val Val Leu Thr Asn Leu Leu Pro Gly Thr Glu Tyr Val Val Ser
       130                 135                 140

Val Ser Ser Val Tyr Glu Gln His Glu Ser Thr Pro Leu Arg Gly Arg
145                 150                 155                 160

Gln Lys Thr Gly Leu Asp Ser Pro Thr Gly Ile Asp Phe Ser Asp Ile
                165                 170                 175

Thr Ala Asn Ser Phe Thr Val His Trp Ile Ala Pro Arg Ala Thr Ile
            180                 185                 190

Thr Gly Tyr Arg Ile Arg His His Pro Glu His Phe Ser Gly Arg Pro
        195                 200                 205

Arg Glu Asp Arg Val Pro His Ser Arg Asn Ser Ile Thr Leu Thr Asn
    210                 215                 220

Leu Thr Pro Gly Thr Glu Tyr Val Val Ser Ile Val Ala Leu Asn Gly
225                 230                 235                 240

Arg Glu Glu Ser Pro Leu Leu Ile Gly Gln Gln Ser Thr Val Ser Asp
                245                 250                 255

Val Pro Arg Asp Leu Glu Val Val Ala Ala Thr Pro Thr Ser Leu Leu
            260                 265                 270

Ile Ser Trp Asp Ala Pro Ala Val Thr Val Arg Tyr Tyr Arg Ile Thr
        275                 280                 285

Tyr Gly Glu Thr Gly Gly Asn Ser Pro Val Gln Glu Phe Thr Val Pro
```

|     |     |     |     |     | 290 |     |     |     |     | 295 |     |     |     |     | 300 |     |     |     |     |
| --- | --- | --- | --- | --- | --- | --- | --- | --- | --- | --- | --- | --- | --- | --- | --- | --- | --- | --- | --- |
| Gly | Ser | Lys | Ser | Thr | Ala | Thr | Ile | Ser | Gly | Leu | Lys | Pro | Gly | Val | Asp |
| 305 |     |     |     |     | 310 |     |     |     |     | 315 |     |     |     |     | 320 |
| Tyr | Thr | Ile | Thr | Val | Tyr | Ala | Val | Thr | Gly | Arg | Gly | Asp | Ser | Pro | Ala |
|     |     |     |     | 325 |     |     |     |     | 330 |     |     |     |     | 335 |     |
| Ser | Ser | Lys | Pro | Ile | Ser | Ile | Asn | Tyr | Arg | Thr | Glu | Ile | Asp | Lys | Pro |
|     |     |     | 340 |     |     |     |     | 345 |     |     |     |     | 350 |     |     |
| Ser | Gln | Met | Gln | Val | Thr | Asp | Val | Gln | Asp | Asn | Ser | Ile | Ser | Val | Lys |
|     |     | 355 |     |     |     |     | 360 |     |     |     |     | 365 |     |     |     |
| Trp | Leu | Pro | Ser | Ser | Ser | Pro | Val | Thr | Gly | Tyr | Arg | Val | Thr | Thr | Thr |
|     |     | 370 |     |     |     | 375 |     |     |     |     | 380 |     |     |     |     |
| Pro | Lys | Asn | Gly | Pro | Gly | Pro | Thr | Lys | Thr | Lys | Thr | Ala | Gly | Pro | Asp |
| 385 |     |     |     |     | 390 |     |     |     |     | 395 |     |     |     |     | 400 |
| Gln | Thr | Glu | Met | Thr | Ile | Glu | Gly | Leu | Gln | Pro | Thr | Val | Glu | Tyr | Val |
|     |     |     |     | 405 |     |     |     |     | 410 |     |     |     |     | 415 |     |
| Val | Ser | Val | Tyr | Ala | Gln | Asn | Pro | Ser | Gly | Glu | Ser | Gln | Pro | Leu | Val |
|     |     |     | 420 |     |     |     |     | 425 |     |     |     |     | 430 |     |     |
| Gln | Thr | Ala | Val | Thr | Asn | Ile | Asp | Arg | Pro | Lys | Gly | Leu | Ala | Phe | Thr |
|     |     | 435 |     |     |     |     | 440 |     |     |     |     | 445 |     |     |     |
| Asp | Val | Asp | Val | Asp | Ser | Ile | Lys | Ile | Ala | Trp | Glu | Ser | Pro | Gln | Gly |
|     | 450 |     |     |     |     | 455 |     |     |     |     | 460 |     |     |     |     |
| Gln | Val | Ser | Arg | Tyr | Arg | Val | Thr | Tyr | Ser | Ser | Pro | Glu | Asp | Gly | Ile |
| 465 |     |     |     |     | 470 |     |     |     |     | 475 |     |     |     |     | 480 |
| His | Glu | Leu | Phe | Pro | Ala | Pro | Asp | Gly | Glu | Glu |
|     |     |     |     | 485 |     |     |     |     | 490 |     |

( 2 ) INFORMATION FOR SEQ ID NO:3:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:3:

Lys Tyr Gly Arg Gly Asp Ser
1               5

( 2 ) INFORMATION FOR SEQ ID NO:4:

( i ) SEQUENCE CHARACTERISTICS:
( A ) LENGTH: 96 base pairs
( B ) TYPE: nucleic acid
( C ) STRANDEDNESS: double
( D ) TOPOLOGY: circular ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

TCGAGCTCGG TACCCGGCCG GGGATCCATC GAGGGTAGGC CTGAATTCAG TAAAACCCTC    60

GATGGATCCT CTAGAGTCGA CCTGCAGGCA AGCTTG    96

POLYPEPTIDES FOR PROMOTING CELL ATTACHMENT

This invention was made with the support of the United States Government, and the United States Government has certain rights in the invention pursuant to National Institutes of Health Grant HL 28235.

CROSS-REFERENCE TO RELATED APPLICATION

The present application is a continuation-in-part of copending application Ser. No. 07/803,623, filed Nov. 27, 1991, which is a continuation-in-part of application Ser. No. 07/725,600, filed July 3, 1991, now abandoned, which is a continuation-in-part of application Ser. No. 07/620,668, filed Dec. 3, 1990, now abandoned, which applications are hereby incorporated by reference.

DESCRIPTION

1. Technical Field

The present invention relates to methods and compositions for promoting cell attachment to substrates. The invention particularly relates to the use of newly identified binding sites of fibronectin for binding to integrin receptors on cells.

2. Background

Regulation of cell adhesive events has broad biomedical implications. For instance, inhibition of cell adhesion may be of benefit in the treatment of thrombotic disorders through inhibition of platelet aggregation, of inflammatory disorders through inhibition of leukocyte adhesion and transmigration, and in malignant disease through inhibition of tumor cell lodgement and metastasis. Conversely, promotion of cell adhesion is, in some cases, desirable. For example, in the seeding of endothelial cells onto vascular grafts, in the stability of medical prostheses, and in promotion of wound healing. Adhesive events are widely recognized to involve interactions of extracellular receptors, i.e., integrin receptors, with substances surrounding the cell, e.g., fibronectin. Integrins are a functionally and structurally related group of receptors that interact with a wide variety of ligands including extracellular matrix glycoproteins, complement and other cells. Integrins participate in cell-matrix and cell-cell adhesion in many physiologically important processes including embryological development, hemostasis, thrombosis, wound healing, immune and non-immune defense mechanisms and oncogenic transformation. See Hynes, *Cell,* 48:549–554 (1987). Several integrins that participate in dynamic cell adhesion bind a tripeptide, arginine-glycine-aspartic acid (RGD), present in their ligand. See Ruoslahti et al., *Science,* 238:491–497 (1987).

Fibronectin is an adhesive glycoprotein found in plasma and on cell surfaces and extracellular matrices. By binding other macromolecules as well as cells, fibronectin promotes anchorage of cells to substrata. Hynes, in Cell Biology of the Extracellular Matrix, Hay ed., Plenum Press, pages 295–334 (1982); Hynes et al., *J. Cell Biol.,* 95:369–77 (1982). Also, fibronectin is known to accumulate at sites of injury and inflammation in vivo [Pettersson et al., *Clin. Immunol. Immunopath,* 11:425–436 (1978); Grinnel et al., *J. Invest. Derm.,* 76:181–189 (1981); Repesh et al., *J. Histochem. Cytochem.,* 30(4):399–408 (1985); Carsons et al., *Arth. Rheum,* 24(10):1261–67 (1981)] and is produced by cells in blood vessel walls at these sites. Clark et al., *J. Exp. Med.,* 156:646–51 (1982); Clark et al., *J. Immunol.,* 126(2):787–93 (1981); Clark et al., *J. Invest. Derm.,* 79:269–76 (1982); Clark et al., *J. Clin Invest.,* 74:1011–16 (1984).

Fibronectin is composed of subunits of variable primary structure [average relative molecular mass of 250 kilodaltons (kDa)]. The subunits are disulfide-linked to form dimers or multimers derived from a pool of similar but nonidentical polypeptides. Hynes, in *Cell Biology of the Extracellular Matrix,* Hay ed., Plenum Press, pages 295–334 (1982); Hynes et al., *Cell Biol.,* 95:369–77 (1982); Schwarzbauer et al., *Proc. Natl., Acad. Sci. USA,* 82:1424–28; Kornblihtt et al., *EMBO J.,* 4(7): 1755–59 (1985). Thus, the term "fibronectin" refers to several species of glycoprotein, some of which are more fully characterized than others.

Two major fibronectin (Fn) classes are plasma fibronectin and cellular fibronectin. Plasma fibronectin (pFn) is secreted by hepatocytes, whereas cellular fibronectin (cFn) is secreted by a variety of cultured cells including endothelial cells and fibroblasts. Jaffe et al., *J. Exp Med.,* 147:1779–91 (1978); Birdwell et al., *Biochem. Biophys. Res. Commun.,* 97(2):574–8 (1980). Despite extensive physical and immunologic similarities, the two classes of fibronectin differ in electrophoretic behavior, solubility, and biologic activities. Tamkun et al., *J. Biol. Chem.,* 258 (7):4641–47 (1983); Yamada et al., *J. Cell Biol.,* 80:492–98 (1979); Yamada et al., *Biochemistry,* 16 (25):2552–59, (1977).

Primary structural differences between plasma and cellular fibronectins have been found by peptide mapping [Hayashi et al., *J. Biol. Chem.,* 256(21):11,292–11,300 (1981)], cDNA cloning [Kornblihtt et al., *EMBO J.,* 4:1755–1759 (1985)], and immunologic techniques [Atherton et al., Cell, 25:133–41 (1981)]. From these data, it has been determined that the primary structure of fibronectin monomer contains three different types of internal repeats known as homology Types I, II and III, having lengths of about 40, 60 and 90 amino acids residues, respectively [Kornblihtt et al., *EMBO J.,* 4:1755–1759 (1985)]. All of the various distinct Fn moieties are produced by a single gene, with differences in primary structure resulting from alternative splicing of the primary mRNA transcript in at least three regions. Kornblihtt et al., *EMBO J.,* 4(7):1755–59 (1985); Schwarzbauer et al., *Proc. Natl. Acad. Sci.* USA, 82:1424–28 (1985); Gutman et al., *Proc. Natl. Acad. Sci.* USA, 84:7179–82 (1987); Schwarzbauer et al., *EMBO J.,* 6(9):2573–80 (1987).

A site containing the Arg-Gly-Asp (RGD) sequence in the 10th Type III repeat of Fn is known to be involved in cell adhesive events. Peptides containing this sequence inhibit certain cell adhesive events, or alternatively, can be used to promote cell adhesion. See, e.g., U.S. Pat. Nos. 4,589,881; 4,661,111; 4,517,686; 4,683,291; 4,578,079; 4,614,517; and 4,792,525.

Recently, site-directed mutagenesis studies of fibronectin have implicated non-RGD sequences as participating in cell adhesion phenomena. [Obara, M. et al. *Cell,* 53:649–57 (1988)]. The proposed second binding site was not defined by this study; however, activity loss data indicated that a second site was involved in adhesion, probably in a synergistic fashion with the RGD sequence. This result helps to explain why other RGD-containing proteins do not bind integrins as well as fibronectin.

In view of the importance of promoting cell adhesion or, conversely, for inhibiting adhesion, non-RGD containing polypeptides suitable for these purposes are desired. In the event such polypeptides are found to complement RGD amino acid residue sequences in cell binding processes, compositions including both RGD sequences and adhesive non-RGD compounds are also desired.

BRIEF SUMMARY OF THE INVENTION

The present invention is for polypeptides that bind to integrin receptors, particularly GPIIb-IIIa, which polypeptides define a binding region (sites) for the integrin that is independent of the well-known RGD sequence of fibronectin (Fn). The new binding sites are located at least fifty amino acid residues upstream (toward the N-terminus) of the RGD sequence of human Fn. The amino acid residue sequence of human Fn is described in Kornblihtt, et al., *EMBO J.*, 4:1755 (1985), which description is incorporated herein by reference. Selected regions of human Fn are depicted in SEQ ID NOs 1 and 2 and include the sequence of fibronectin described by Kornblihtt et al.

In one embodiment, the present invention contemplates a polypeptide having a length of no more than about 200 amino acid residues. The peptide binds GPIIb-IIIa, includes an amino acid residue sequence represented by the formula shown in SEQ ID NO (2:248–274) corresponding to Fn residues 1410–1436, and does not include the Fn sequence RGD.

Preferably, the polypeptide includes an amino acid residue sequence represented by the formula shown in SEQ ID NO (2:197–274) corresponding to Fn residues 1359–1436. Particularly preferred is a polypeptide having an amino acid residue sequence, the SEQ ID NO and corresponding residue positions of which are shown in parenthesis, selected from the group consisting of: (2:248–274), (2:197–274), (2:217–274) and (2:73–274).

In a preferred embodiment of the invention the instant polypeptides will have an amino acid residue sequence represented by the formula B-X-Z where X is the amino acid residue sequence at residues 1410–1436 (SEQ ID NO 2:248–274) of human Fn, B is an $NH_2$ group or N-terminal sequence of amino acids no more than 150 residues in length, and Z is a COOH group or C-terminal sequence of amino acids no more than 150 residues in length, with the proviso that X-Z does not correspond to the region of human fibronectin including RGD.

The instant polypeptides can bind to GPIIb-IIIa independently or in concert with an RGD-containing peptide. When binding is complementary with an RGD sequence the RGD sequence may be incorporated in the same protein as an instant polypeptide or it may be provided in a distinct peptide.

Also contemplated within the invention are methods for attaching cells, e.g., endothelial cells, to a substrate in which the method comprises contacting cells expressing GPIIb-IIIa with the substrate comprising the instant polypeptides affixed to a solid matrix and maintaining the contact for a predetermined time sufficient for the GPIIb-IIIa to bind the polypeptides. Use of the polypeptide-substrate is contemplated in skin grafting and prosthesis.

Also contemplated are vectors for expressing the instant polypeptides and fusion proteins containing one-or more of the polypeptides. One embodiment of the invention allows ready purification of the polypeptides by generating maltose binding protein (MBP) fusion products of the polypeptides.

A still further embodiment contemplates antibody compositions that immunoreact with the instant polypeptides which can competitively inhibit Fn or fibrinogen (Fg) binding to GPIIb-IIIa. The instant polypeptides may also be used to inhibit Fn or Fg binding to GPIIb-IIIa.

Thus, the present invention affords novel polypeptides and related compositions and methods which promote cell attachment and/or inhibit cell adhesion.

BRIEF DESCRIPTION OF THE DRAWINGS

In the drawings, forming a portion of this disclosure.

DETAILED DESCRIPTION OF THE INVENTION

A. Definitions

Figure 1A:
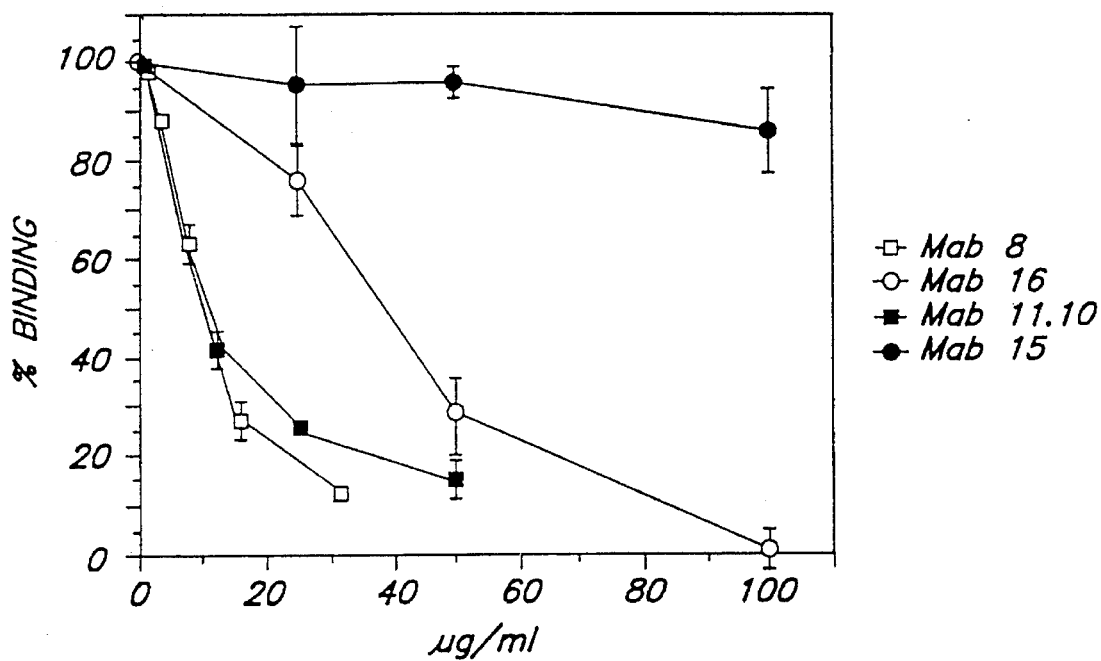
FIG. 1A is a graph that shows the effect on binding of Fn to immobilized GPIIb-IIIa by increasing concentrations (μg/ml) of monoclonal antibodies (MAbs) raised to Fn according to the principles of the present invention. The data is expressed as a percent of binding as described in the Examples.

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 C.F.R. §1.822(b)(2)), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |

-continued

TABLE OF CORRESPONDENCE

| SYMBOL | | |
|---|---|---|
| 1-Letter | 3-Letter | AMINO ACID |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left to right orientation in the conventional direction of amino-terminus to carboxy-terminus. In addition, the phrase "amino acid residue" is broadly defined to include the amino acids listed in the Table of Correspondence and modified and unusual amino acids, such as those listed in 37 C.F.R. §1,822(b)(4), and incorporated herein by reference. Furthermore, it should be noted that a dash at the beginning or end of an amino acid residue sequence indicates a peptide bond to a further sequence of one or more amino acid residues or to an amino-terminal group such as $NH_2$ or to a carboxy-terminal group such as COOH.

Antibody: a polypeptide which chemically binds to a haptenic group, i.e., ligand. Antibodies, as used herein, are immunoglobulin molecules and immunologically active fragments of immunoglobulin molecules. Such portions known in the art as Fab, Fab'; F(ab')$_2$ and F$_v$ are included. Typically, antibodies bind ligands that range in size from about 6 to about 34 Å with association constants in the range of about $10^4$ to $10^{10}$ M$^{-1}$ and as high as $10^{12}$ M$^{-1}$. Antibodies may be polyclonal or monoclonal (MAb). Antibodies can bind a wide range of ligands, including small molecules such as steroids and prostaglandins, biopolymers such as nucleic acids, proteins and polysaccharides, and synthetic polymers such as polypropylene. An "antibody combining site" is that structural portion of an antibody molecule comprised of a heavy and light chain variable and hypervariable regions that specifically binds (immunoreacts with) antigen. The term "immunoreact" in its various forms is used herein to refer to binding between an antigenic determinant-containing molecule and a molecule containing an antibody combining site such as a whole antibody molecule or a portion thereof. An "antigenic determinant" is the actual structural portion of the antigen that is immunologically bound by an antibody combining site. The term is also used interchangeably with "epitope".

Ligand: a molecule that contains a structural portion that is bound by specific interaction with a particular receptor molecule.

Oligonucleotide or Polynucleotide: a polymer of single or double stranded nucleotides. As used herein "oligonucleotide" and its grammatical equivalents will include the full range of nucleic acids. An oligonucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art.

Polypeptide or Peptide: a linear series of at least two amino acid residues in which adjacent residues are connected by peptide bonds between the alpha-amino group of one residue and the alphacarboxy group of an adjacent residue.

Protein: refers to a linear series of more than 50 amino acid residues in which adjacent residues are connected via peptide linkages.

Receptor: a biologically active proteinaceous molecule that specifically binds to (or with) other molecules (ligands). Receptors can be glycosylated.

Vector: a DNA molecule capable of autonomous replication in a cell and to which a DNA segment, e.g., gene or polynucleotide, can be operatively linked so as to bring about replication of the attached segment. Vectors capable of directing the expression of DNA segments (genes) encoding one or more proteins are referred to herein as "expression vectors". Vectors also allow cloning of cDNA (complementary DNA) from mRNAs produced using reverse transcriptase.

B. Polypeptides

The polypeptides of the present invention include an amino acid residue sequence corresponding to a region of fibronectin (Fn) and are referred to as fibronectin-derived polypeptides or Fn polypeptides.

The Fn used in this invention was isolated from fresh human citrated plasma by affinity chromatography on gelatin-sepharose according to the methods described by Plow et al., *J. Biol. Chem.*, 256:9477–9482 (1981) and in U.S. Pat. No. 4,589,981. The isolated Fn yielded a single band on SDS-PAGE under nonreducing conditions and a closely spaced doublet of 215,000 to 230,000 molecular weight under reducing conditions. Hereinafter, Fn refers to intact isolated Fn as described above and in Example 9b(1).

Typically, the subject polypeptides corresponding to a region of Fn will not contain an RGD sequence, thereby presenting potential binding sites for ligands that have a three-dimensional structure different from the RGD sequence of Fn. It is preferred that the entire sequence of the polypeptide represent a portion of Fn.

In one embodiment, a polypeptide of this invention has a length of no more than about 200 amino acid residues and includes an amino acid residue sequence represented by the formula shown in SEQ ID NO (2:248–274) corresponding to Fn residues 1410–1436. The polypeptide inhibits fibronectin binding to GPIIb-IIIa, and its sequence does not include the Fn sequence RGD. Preferably, the polypeptide includes an amino acid residue sequence represented by the formula shown in SEQ ID NO (2:197–274) corresponding to Fn residues 1359–1436.

In one embodiment, a polypeptide has an amino acid residue sequence that corresponds to the sequence of fibronectin shown in SEQ ID NO 2.

A preferred polypeptide has an amino acid residue sequence, the SEQ ID NO and corresponding residue positions of which are shown in parenthesis, represented by a formula in a SEQ ID NO selected from the group consisting of (2:248–274), (2:197–274), (2:217–274) and (2:73–274).

Preferably, the amino- and carboxy-terminal of the formula are amino- and carboxy-terminal groups, respectively, with the preferred amino-terminal group being $NH_2$, and the preferred carboxy-terminal group being COOH.

Alternatively, the termini can have additional amino acid residue sequences, such as in a fusion protein. A fusion protein is defined herein as a polypeptide comprised of at least two different amino acid residue sequences operatively linked into a single polypeptide, where the two different sequences are derived from separate natural proteins, or from two domains of the same natural protein which domains are not found operatively linked to form the resulting sequence in nature.

In this embodiment of the invention the instant polypeptides will have an amino acid residue sequence represented by the formula B-X-Z where X is the amino acid residue sequence at residues 1410–1436 (SEQ ID NO 2:248–274) of human Fn, B is an $NH_2$ group or N-terminal sequence of amino acids typically no more than about 150 residues in length,, and Z is a COOH group or C-terminal sequence of amino acids typically no more than about 150 residues in length, with the proviso that X-Z does not correspond to a region of human fibronectin including RGD.

In one embodiment of the invention the polypeptide can have a maltose-binding protein (MBP) covalently bonded to the N-terminus of the selected Fn sequence. The MBP region of the fusion protein strongly binds to immobilized amylose (starch) which facilitates purification of the desired protein from contaminants, such as non-MBP containing proteins. The MBP fragment may be directly bonded to the selected Fn fragment or intervening amino acid residues may be provided between the MBP and polypeptide regions. Exemplary fusion protein are described herein.

In one embodiment, the instant polypeptides are not glycosylated, i.e., they are produced directly by peptide synthesis techniques or are produced in a procaryotic cell transformed with a recombinant DNA of the present invention. Eucaryotically produced peptide molecules are typically glycosylated.

It should be understood that a subject polypeptide need not be identical to the amino acid residue sequence of Fn, so long as the subject polypeptides are able to compete for binding sites of GPIIb-IIIa.

A subject polypeptide includes any analog, fragment or chemical derivative of a polypeptide whose amino acid residue sequence is shown herein so long as the polypeptide is able to compete for binding sites of GPIIb-IIIa. Therefore, a present polypeptide can be subject to various changes, insertions, deletions and substitutions, either conservative or nonconservative, where such changes provide for certain advantages in its use.

In this regard, a polypeptide of this invention corresponds to, rather than is identical to, the sequence of Fn where one or more changes are made and it retains the ability to compete for binding sites in one or more of the assays as defined herein.

The term "analog" includes any polypeptide having an amino acid residue sequence substantially identical to a sequence specifically shown herein in which one or more residues have been conservatively substituted with a functionally similar residue and which displays the ability to inhibit binding as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

Particularly preferred modifications are those modifications designed to increase the stability of the polypeptide in solution, and therefore serve to prolong half life of the polypeptides in solutions, particularly biological fluids such as blood, plasma or serum. Exemplary modifications are those that block susceptibility to proteolytic activity in the blood. Thus a polypeptide can have a stabilizing group at one or both termini. Typical stabilizing groups include amido, acetyl, benzyl, phenyl, tosyl, alkoxycarbonyl, alkyl carbonyl, benzyloxycarbonyl and the like end group modifications. Additional modifications include using a "L" amino acid in place of a "D" amino acid at the termini, cyclization of the polypeptide, and amide rather than amino or carboxy termini to inhibit exopeptidase activity.

Polypeptides of the present invention also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

When a polypeptide of the present invention has a sequence that is not identical to the sequence of Fn, it is typically because one or more conservative or non-conservative substitutions have been made, usually no more than about 30 number percent, and preferably no more than 10 number percent of the amino acid residues are substituted.

"Substantially homologous" means that a particular subject sequence or molecule, for example, a mutant sequence, varies from a reference sequence by one or more substitutions, deletions, or additions, the net effect of which does not result in an adverse functional dissimilarity between reference and subject sequences. For purposes of the present invention, amino acid sequences having greater than 90 percent similarity, equivalent biological activity, and equivalent expression characteristics are considered substantially homologous and are included within the scope of a polypeptide of this invention.

Amino acid sequences having greater than 40 percent similarity are considered substantially similar. For purposes of determining homology or similarity, truncation or internal deletions of the reference sequence should be disregarded, as should subsequent modifications of the molecule, e.g., glycosylation. Sequences having lesser degrees of homology and comparable bioactivity are considered equivalents.

Additional residues may also be added at either terminus of an polypeptide of this invention for the purpose of providing a "linker" by which the polypeptides of this invention can be conveniently affixed to a label or solid matrix, or carrier. Preferably, the linker residues do not form epitopes which are cross reactive with Fn, i.e., are not sufficiently similar in structure to a Fn polypeptide as to produce cross-reacting antibodies.

Labels, solid matrices and carriers that can be used with the polypeptides of this invention are described hereinbelow.

Amino acid residue linkers are usually at least one residue and can be 40 or more residues, more often 1 to 10 residues, but do not form epitopes cross-reactive with a Fn polypeptide of this invention. Typical amino acid residues used for linking are tyrosine, cysteine, lysine, glutamic and aspartic acid, or the like. In addition, a subject polypeptide can differ, unless otherwise specified, from the natural sequence of the corresponding protease by the sequence being modified by terminal-$NH_2$ acylation, e.g., acetylation, or thioglycolic acid amidation, by terminal-carboxylamidation, e.g., with ammonia, methylamine, and the like terminal modifications.

When coupled to a carrier to form what is known in the art as a carrier-hapten conjugate, a polypeptide of the present invention is capable of inducing antibodies that immunoreact with Fn. In view of the well established principle of immunologic cross-reactivity, the present invention therefore contemplates antigenically related variants of a polypeptide of this invention. An "antigenically related variant" is a subject polypeptide that is capable of inducing antibody molecules that immunoreact with a polypeptide of this invention and immunoreact with Fn.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

A polypeptide of the present invention also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis", W. H. Freeman Co. , San Francisco, 1969; M. Bodanszky, et al., "Peptide Synthesis", John Wiley & Sons, Second Edition, 1976 and J. Meienhofer, "Hormonal Proteins and Peptides", Vol 2 p. 46, Academic Press (New York), 1983 for solid phase peptide synthesis, and E. Schroder and K. Kubke, "The Peptides", Vol 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

Alternatively, the instant polypeptides may be synthesized by recombinant DNA techniques. A number of different nucleotide sequences may code for a particular amino acid residue sequence due to the redundancy of the genetic code. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

C. DNA Segments

Contemplated within the present invention are deoxyribonucleic acid (DNA) molecules that define a gene coding for, i.e., capable of expressing, a subject polypeptide or a subject chimeric polypeptide. DNA molecules that encode the subject polypeptides can easily be synthesized by chemical techniques, for example, the phosphotriester method of Matteucci et al., *J. Am. Chem. Soc.*, 103:3185 (1981). Of course, by chemically synthesizing the coding sequence, any desired modifications can be made simply by substituting the appropriate bases for those encoding the native amino acid residue sequence.

A DNA molecule that includes a DNA sequence encoding a subject polypeptide can be prepared by operatively linking (ligating) appropriate restriction fragments from each of the above deposited plasmids using well known methods. The DNA molecules of the present invention produced in this manner typically have cohesive termini, i.e., "overhanging" single-stranded portions that extend beyond the double-stranded portion of the molecule. The presence of cohesive termini on the DNA molecules of the present invention is preferred.

Also contemplated by the present invention are ribonucleic acid (RNA) equivalents of the above described DNA molecules.

Preferred DNA segments will encode polypeptides that include an amino acid residue sequence corresponding to the sequence of Fn at Fn residues 1410–1436 shown in SEQ ID NO 2 at residues 248–274. Additional DNA segments encode other polypeptides and fusion proteins of this invention.

D. Vectors

The present invention further contemplates a recombinant DNA molecule comprising a vector operatively linked, for replication and/or expression, to a subject DNA segment, i.e., a DNA molecule defining a gene coding for a subject polypeptide or a subject fusion protein.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of the subject chimeric polypeptide gene included in DNA segments to which it is operatively linked.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the subject chimeric polypeptide gene in a bacterial host cell, such as *E. coli*, transformed therewith. A promoter is an expression control element formed by a DNA sequence that permits binding of RNA polymerase and transcription to occur. Promoter sequences compatible with bacterial hosts, such as a tac promoter, are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.) and pPL and pKK223 available from Pharmacia (Piscataway, N.J.).

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-lpML2d (International Biotechnologies, Inc.), and pTDT1 (ATCC, #31255).

In preferred embodiments, the eucaryotic cell expression vectors used to construct the recombinant DNA molecules of the present invention include a selection marker that is effective in an eucaryotic cell, preferably a drug resistance selection marker. A preferred drug resistance marker is the gene whose expression results in neomycin resistance, i.e., the neomycin phosphotransferase (neo) gene. Southern et al., *J. Mol. Appl. Genet.*, 1:327–341 (1982).

The use of retroviral expression vectors to form the rDNA of the present invention is also contemplated. As used herein, the term "retroviral expression vector" refers to a DNA molecule that includes a promoter sequence derived from the long terminal repeat (LTR) region of a retrovirus genome.

In preferred embodiments, the expression vector is typically a retroviral expression vector that is preferably replication-incompetent in eucaryotic cells. The construction and use of retroviral vectors has been described by Sorge, et al., *Mol. Cell. Biol.*, 4:1730–37 (1984).

A variety of methods have been developed to operatively link DNA to vectors via complementary cohesive termini. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase of *E. coli* DNA polymerase I, enzymes that remove protruding, 3', single-stranded termini with their 3'–5' exonucleolytic activities and fill in recessed 3' ends with their polymerizing activities. The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies, Inc. (New Haven, Conn.).

Also contemplated by the present invention are RNA equivalents of the above described recombinant DNA molecules.

Preferred vectors will include a DNA segment that encodes a polypeptide of the present invention. Exemplary vectors include pIH821 and pPR734 (FIG. 2), for preparing MBP fusion proteins according to the principles of this invention.

E. Transformation of Hosts

The present invention also relates to host cells transformed with a recombinant DNA (rDNA) molecule of the present invention preferably an rDNA capable of expressing a subject chimeric polypeptide. The host cell can be either procaryotic or eucaryotic. Bacterial cells are preferred procaryotic host cells and typically are a strain of *E. coli* such as, for example, the *E. coli* strain DH5 available from Bethesda Research Laboratories, Inc., Bethesda, Md. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61 and NIH Swiss mouse embryo cells NIH/3T3 available from the ATCC as CRL 1658. Transformation of appropriate cell hosts with a recombinant DNA molecule of the present invention is accomplished by well known methods that typically depend on the type of vector used. With regard to transformation of procaryotic host cells, see, for example, Cohen et al., *Proc. Natl. Acad. Sci. USA*, 69:2110 (1972); and Maniatis et al., *Molecular Cloning, A Laboratory Manual*, Cold Spring Harbor Laboratory, Cold Spring Harbor, N.Y. (1982). With regard to transformation of vertebrate cells with retroviral vectors containing rDNAs. See, for example, Sorge et al., *Mol. Cell. Biol.*, 4:1730–37 (1984); Graham et al., *Virol.*, 52:456 (1973); and Wigler et al., *Proc. Natl. Acad. Sci. USA*, 76:1373–76 (1979).

Successfully transformed cells, i.e., cells that contain a recombinant DNA molecule of the present invention, can be identified by well known techniques. For example, cells resulting from the introduction of an rDNA of the present invention can be cloned to produce monoclonal colonies. Cells from those colonies can be harvested, lysed and their DNA content examined for the presence of the rDNA using a method such as that described by Southern, *J. Mol. Biol.*, 98–503 (1975) or Berent et al., *Biotech.*, 3:208 (1985).

In addition to directly assaying for the presence of rDNA, successful transformation can be confirmed by well known immunological methods when the rDNA is capable of directing the expression of a subject chimeric polypeptide. Samples of cells suspected of being transformed are harvested and assayed for the presence of polypeptide antigenicity using anti-Fn antibodies.

In addition to the transformed host cells themselves, the present invention also contemplates a culture of those cells, preferably a monoclonal (clonally homogeneous) culture, or a culture derived from a monoclonal culture, in a nutrient medium.

F. Expression and Purification

Nutrient media useful for culturing transformed host cells are well known in the art and can be obtained from several commercial sources. In embodiments wherein the host cell is mammalian, a "serum-free" medium is preferably used.

Methods for recovering an expressed protein from a culture are well known in the art and include fractionation of the protein-containing portion of the culture using well known biochemical techniques. For instance, the methods of gel filtration, gel chromatography, ultrafiltration, electrophoresis, ion exchange, affinity chromatography and the like, such as are known for protein fractionations, can be used to isolate the expressed proteins found in the culture. In addition, immunochemical methods, such as immunoaffinity, immunoadsorption and the like can be performed using well known methods. A preferred purification method employs immobilized Mabs to Fn.

G. Therapeutic Methods and Compositions

A subject polypeptide can be used in a composition for promoting the attachment (adhesion) of cells to a substrate. Based on the ability of a subject polypeptide to bind with an integrin on the cells, the subject polypeptide provides a means for binding to the receptor, and therefore can be used to promote cell attachment activity when the polypeptide is immobilized onto a substrate. A composition containing a subject polypeptide is used to treat a substrate and thereby to immobilize the polypeptide contained in the composition onto the substrate.

The substrate can be any solid-matrix having a surface on which cell adhesion promoting activity is desired and includes containers for cell culture, medical devices, prosthetic devices, synthetic resin fibers, blood vessels or vascular grafts, percutaneous devices, artificial organs, and the like. The surface can additionally be comprised of glass, a synthetic resin, nitrocellulose, polyester, agarose, collagen or a long chain polysaccharide.

Immobilization of polypeptides onto substrate can be accomplished by a variety of means and depends, inter alia, on the substrate and the mechanism of immobilization desired. Methods for polypeptide immobilization or coupling to the substrate are well known in the art and typically involve covalent linkages between a thiol or amino group on the polypeptide to a reactive group present on the substrate. For examples of polypeptide immobilization methods see Aurameas et al., *Scand J. Immunol.*, Vol. 8 Suppl. 7:7–23 (1978); U.S. Pat. Nos. 4,493,795, 4,578,079 and 4,671,950; Klipstein et al., *J. Infect. Dis.*, 147:318–326 (1983) and Liu et al., *Biochem.*, 80:690 (1979). For examples of the use of cell adhesion promoting polypeptides see U.S. Pat. No. 4,578,079.

Also contemplated are prosthetic and medical devices that make use of the substrata to attach cells to the surface in vivo or to promote growth of cells on a particular surface prior to grafting. For example, endothelial cell growth can be induced on prosthetic blood vessels or vascular grafts, such as those woven or knitted from polyester fibers. Such devices can be useful for wound closure and healing following accidents or surgery. In such cases it may be useful to couple the polypeptides to other biological molecules, such as collagen, glycosaminoglycans, etc. The coupling can be facilitated by chemical crosslinking, e.g., by disulfide bridges. Surfaces of prosthetic devices can also be coated with the instant polypeptides, particularly when the devices are intended for use temporarily in the body, e.g., for insertion into blood vessels or into the peritoneal cavity.

The subject polypeptides can be provided within a wide variety of compositions. Thus, the polypeptide compositions can comprise one or more polypeptides as well as a suitable application medium, such as a gel, salve, lotion, colloid or powder. The composition is applied to the substrate using conventional means and the cells desired to be attached are applied using techniques well-known to the skilled practitioner.

In one embodiment relying on the inhibitory capacity of a polypeptide or fusion protein of this invention, method is contemplated for inhibiting the binding of fibronectin or fibrinogen to platelet glycoprotein GPIIb-IIIa comprising contacting GPIIb-IIIa in an aqueous solution with a polypeptide or fusion protein according to this invention in an amount sufficient to inhibit the binding event. Amounts sufficient for inhibition are shown by the teachings herein, and are in the range of micromolar to millimolar.

A related embodiment contemplates modulating the adhesion in vivo of cells presenting an integrin receptor recognized by the polypeptide, particularly for modulating the binding interaction of GPIIb-IIIa-bearing cells to fibronectin. For instance, a subject polypeptide can be used in a pharmaceutically acceptable composition that, when administered to a human subject in an effective amount, is capable of competitively inhibiting the binding of fibronectin or fibrinogen to GPIIb-IIIa, or inhibiting the aggregation of platelets. That inhibition is believed to result in a decreased rate of thrombus formation. Thus, in vivo administration of a subject polypeptide can be used to modulate any physiological response initiated by fibronectin or fibrinogen binding to GPIIb-IIIa such as coagulation and some inflammatory responses.

Insofar as the present invention demonstrates that a fusion protein containing a Fn polypeptide as defined herein is also shown to inhibit fibronectin or fibrinogen binding to GPIIb-IIIa and to directly bind GPIIb-IIIa, a fusion protein of this invention can be utilized in the same manner as a Fn polypeptide.

In another embodiment, the normal cellular adhesion functions of a cell bearing an integrin on its surface can be inhibited or modulated by intravenous administration of an effective amount of a pharmaceutically acceptable composition comprising a polyclonal or monoclonal antibody of this invention that immunoreacts with a polypeptide or fusion protein of this invention.

Insofar as polyclonal or monoclonal antibodies can be used therapeutically to modulate cell adhesion-mediated events, the present invention also contemplates the use of a subject polypeptide or fusion protein to neutralize the modulating effect of therapeutically administered antibodies, e.g., as an antidote for the anti-polypeptide antibody. The choice of polypeptide to be administered as an antidote depends upon the antibody-to be neutralized, and requires that the administered polypeptide have the capacity to immunoreact with the administered antibody.

The polypeptide- or antibody molecule-containing compositions administered take the form of solutions or suspensions, however, polypeptides can also take the form of tablets, pills, capsules, sustained release formulations or powders.

A therapeutic composition typically contains an amount of at least 0.1 weight percent of active ingredient, i.e., a polypeptide or antibody of this invention, per weight of total therapeutic composition. A weight percent is a ratio by weight of active ingredient to total composition. Thus, for example, 0.1 weight percent is 0.1 grams of polypeptide per 100 grams of total composition.

Stated differently, a therapeutic composition typically contains about 0.1 micromolar (μM) to about 1.0 molar (M) of polypeptide as active ingredient, preferably about 1.0 to about 100 millimolar (mM), whereas the antibody molecule-containing compositions typically contain about 0.1 to about 20 milligram of antibody as active ingredient per milliliter of therapeutic composition, and preferably about 1 mg/ml to about 10 mg/ml.

A therapeutically effective amount of a polypeptide or fusion protein of this invention is typically an amount such that when administered in a physiologically tolerable composition or contacted with a target GPIIb-IIIa is sufficient to achieve a concentration of from about 0.1 micromolar (uM) to about 1000 uM, and preferably from about 0.5 uM to about 100 uM.

A therapeutically effective amount of an antibody of this invention is typically an amount of antibody such that when administered in a physiologically tolerable composition or contacted with a target GPIIb-IIIa is sufficient to achieve a concentration of from about 0.1 microgram (ug) per milliliter (ml) to about 100 ug/ml, preferably from about 1 ug/ml to about 5 ug/ml, and usually about 5 ug/ml.

The preparation of a therapeutic composition that contains polypeptides or antibody molecules as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient as are well known. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide or antibody can be formulated into the therapeutic composition as neutralized pharmaceutically acceptable salt forms. Pharmaceutically acceptable salts include the acid addition salts (formed with the free amino groups of the polypeptide or antibody molecule) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide- or antibody-containing compositions are conventionally administered intravenously, as by injection of a unit dose, for example. The term "unit dose" when used in reference to a therapeutic composition of the present invention refers to physically discrete units suitable as unitary dosages for humans, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject to utilize the active ingredient, and degree of inhibition of receptor-ligand binding desired. Precise amounts of active ingredient required to be administered depend on the judgment of the practitioner and are peculiar to each individual. However, suitable dosage ranges are of the order of one to several milligrams of active ingredient per individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain therapeutically effective concentrations in the blood are contemplated. For a subject polypeptide, therapeutically effective blood concentrations are in the range of about 1.0 mM to about 10 mM, preferably about 50 mM to about 1.0 mM. Whenever, the subject polypeptides are used for promoting attachment of cells, e.g., to bind endothelial cells, such compositions will typically have a higher concentration than those taken internally.

A therapeutically effective amount of a polypeptide of this invention is typically an amount of polypeptide such that when administered in a physiologically tolerable composition is sufficient to achieve a plasma concentration of from about 1 micromolar (uM) to about 100 millimolar (mM), and preferably from about 10 uM to about 100 uM.

A therapeutically effective amount of an antibody of this invention is typically an amount of antibody such that when administered in a physiologically tolerable composition is sufficient to achieve a plasma concentration of from about 0.1 microgram (ug) per milliliter (ml) to about 100 ug/ml, and preferably from about 1 ug/ml to about 5 ug/ml.

H. Antibodies and Monoclonal Antibodies

A reagent of the instant invention is a molecule that specifically binds an epitope of fibronectin (Fn) defined by a polypeptide or fusion protein of this invention. As used herein, the term "specific binding" and its grammatical equivalents refers to a non-random binding reaction between a receptor and a ligand molecule. Illustrative of a specifically-bound receptor-ligand complex as contemplated herein is that between platelet receptor GPIIb-IIIa and ligand Fn at the platelet surface. Other reagents known to specifically bind Fn include polyclonal and monoclonal antibodies raised against Fn and antigenic fragments thereof. Thus, suitable antibodies for producing an antibody of this invention include native antibodies for Fn and antibodies raised against antigenic determinants of Fn such as those defined by the polypeptides of this invention.

The different functional regions of fibronectin can be effectively probed by the use of antibodies to the fibronectin molecule. Thus, antibodies raised to fibronectin can be screened for their ability to bind to (immunoreact) various polypeptide fragments of fibronectin. When the antibody composition studied binds with a given fragment, the fragment is identified as presenting an epitope for the antibody. In this way, the different regions of the protein molecule which are recognized by a given antibody molecule are identified.

The instant Fn polypeptides additionally bind preferentially to their receptors. As used herein, a reagent molecule of the instant invention is regarded as "preferentially binding" a target species in the assay when the reagent more strongly associates with the target molecule than with other species present in the assay. Thus, the reaction of reagent molecule with target generally will have a greater association constant than the reaction of reagent with any other species present in the assay. Typically, a reagent herein will "preferentially" bind its target species when the binding affinity of the reagent for target is 2–3 fold greater, and preferably at least 10 times greater, than the corresponding affinity of the reagent for another species. Thus, an antibody molecule immunoreactive with Fn will preferably have a ten fold greater affinity to Fn than to control peptides. Conversely, Fn preferably binds an antibody molecule of this invention more than ten times greater than control antibody molecules.

Thus an antibody composition of this invention comprises antibody molecules that (1) inhibit fibronectin binding to GPIIb-IIIa, and that (2) immunoreact with fibronectin and with a polypeptide or fusion protein of this invention.

An antibody molecule of this invention does not immunoreact with the polypeptide having the amino acid residue sequence shown in SEQ ID NO 2 from residue 1–217, and does not immunoreact with a fusion protein having a fibronectin sequence consisting essentially of the sequence shown in SEQ ID NO 2 from residue 1–217.

A fusion protein having a fibronectin sequence "consisting essentially of" a recited sequence means, in its art recognized form, that no substantial additions or deletions to the fibronectin portion of the fusion protein are contemplated as would change the basic immunoreactivity profile of the fusion protein. This requirement is shown particularly clearly by the difference in reactivity of FnI-8 and FnI-11 for the fusion protein having the sequence shown in SEQ ID NO 2 from residues 248–354, namely that FnI-8 immunoreacts with Fn(1410–1516)-MBP or with the 11.5 kDa pepsin fragment of fibronectin but FnI-11 does not.

Thus in one embodiment, the invention contemplates an antibody composition wherein the antibody molecules immunoreact with a fusion protein having the fibronectin amino acid residue sequence consisting essentially of the sequence shown SEQ ID NO 2 from residues 248–274, that correspond to Fn residues 1410–1436, and preferably immunoreacts with the Fn 11.5 kDa pepsin fragment having the sequence shown in SEQ ID NO 2 from residues 248–354, corresponding to Fn residues 1410–1516. Exemplary is the monoclonal antibody FnI-8.

In another embodiment, the invention contemplates an antibody composition wherein the antibody molecules immunoreact with a fusion protein having the fibronectin amino acid residue sequence consisting essentially of the sequence shown in SEQ ID NO 2 from residues 197–274, that correspond to Fn residues 1359–1436, and preferably immunoreacts with the fusion protein Fn(1235–1436)-MBP, but does not immunoreact with the Fn 11.5 kDa pepsin fragment having Fn residues 1410–1516. Exemplary are the monoclonal antibodies FnI-11 and FnI-16.

A preferred antibody as contemplated herein is typically produced by immunizing a mammal with an inoculum containing Fn, or polypeptide fragments thereof, from a preselected host animal, thereby inducing in the mammal antibody molecules having the appropriate immunospecificity for the target antigen. The antibody molecules are then collected from the mammal and screened to the extent desired by well known techniques such as, for example, by immunoaffinity for immobilized Fn. Furthermore, an antibody of this invention can be screened for its ability to inhibit binding of a Fn ligand to a GPIIb-IIIa receptor using standard competitive inhibition assays, such as are described in the Examples. The antibody composition so produced can be used inter alia, in the diagnostic methods and systems of the present invention to detect the antigen in a bodily fluid sample.

An antibody of this invention therefor immunoreacts with the GPIIb-IIIa binding site on Fn as defined herein and thereby inhibits for binding to its native receptor GPIIb-IIIa, providing its utility as reagent for inhibiting Fn binding to GPIIb-IIIa.

Thus, a preferred polyclonal antibody is characterized as having the ability to immunoreact with a Fn subunit and thereby inhibit the capacity of the Fn to specifically bind to its receptor, preferably the Fn receptor GPIIb-IIIa. Thus, a subject polyclonal antibody is useful to inhibit, and thereby modulate, either in vivo or in vitro, the adhesion of cells which contain integrin receptors that bind to Fn.

A polyclonal antibody of the present invention is typically produced by immunizing a mammal with an inoculum of the present invention, preferably an inoculum containing a peptide incorporating an amino acid residue sequence located at least 50 amino acids upstream of RGD. The antibody molecules are then collected from the mammal and isolated to the extent desired by well known techniques such as, for example, by immunoaffinity chromatography using the immunizing polypeptide in the solid phase. The polyclonal antibody so produced can be used in, inter alia, the diagnostic methods and systems of the present invention to discriminate between Fn and other proteins or between Fn fragments containing epitopes of the antibodies and other fragments, etc. The antibodies can also be used in therapeutic methods for the purpose of modulating cell adhesion, such as inhibiting platelet adhesion.

Monoclonal antibodies (Mabs) to Fn are also contemplated by the present invention. The phrase "monoclonal antibody composition" in its various grammatical forms refers to a population of antibody molecules that contain only one species of antibody combining site capable of immunoreacting with a particular antigen. The instant Mab composition thus typically displays a single binding affinity for any antigen with which it immunoreacts. A monoclonal antibody composition may therefore contain an antibody molecule having a plurality of antibody combining sites, each immunospecific for a different antigen, e.g., a bispecific monoclonal antibody.

Mabs of the present invention are typically composed of antibodies produced by clones of a single cell, called a hybridoma, that secretes (produces) but one kind of antibody molecule. The hybridoma cell is formed by fusing an antibody-producing cell and a myeloma or other self-perpetuating cell line. Such antibodies were first described by Kohler and Milstein, *Nature*, 256:495–497 (1975), which description is incorporated by reference.

A monoclonal antibody can also be produced by methods well known to those skilled in the art of producing chimeric antibodies. Those methods include isolating, manipulating, and expressing the nucleic acid that codes for all or part of an immunoglobulin variable region including both the portion of the variable region comprising the variable region of immunoglobulin light chain and the portion of the variable region comprising the variable region of immunoglobulin heavy chain. Methods for isolating, manipulating, and expressing the variable region coding nucleic acid in procaryotic and eucaryotic hosts are disclosed in Robinson et al., PCT Publication No. WO 89/0099; Winter et al., European Pat. Publication No. 0239400; Reading, U.S. Pat. No. 4,714,681; Cabilly et al., European Patent Publication No. 0125023; Sorge et al., *Mol. Cell Biol.,* 4:1730–1737 (1984); Beher et al., *Science,* 240:1041–1043 (1988); Skerra et al., *Science,* 240:1030–1041 (1988); and Orlandi et al., *Proc. Natl. Acad. Sci. USA,* 86:3833–3837 (1989). Typically the nucleic acid codes for all or part of an immunoglobulin variable region that binds a preselected antigen (ligand). Sources of such nucleic acid are well known to one skilled in the art and, for example, may be obtained from a hybridoma producing a monoclonal antibody that binds the preselected antigen, or the preselected antigen may be used to screen an expression library coding for a plurality of immunoglobulin variable regions, thus isolating the nucleic acid.

Preferred monoclonal antibodies immunoreact with free Fn or polypeptide fragments thereof with the immunospecificities defined herein. The antibodies may also immunoreact with Fn fragments immobilized on substrates or bound to a ligand, such as GPIIb-IIIa, as long as the Mab epitope(s) is not occluded.

The present invention also contemplates a method of forming a monoclonal antibody molecule that immunoreacts with a region of Fn as defined herein and is capable of inhibiting fibronectin binding to GPIIb-IIIa. The method comprises the steps of:

(a) Immunizing an animal with Fn, or a Fn polypeptide or Fn fusion protein of this invention in the form of an immunogen. Preferably, where the immunogen in a polypeptide, it is a homologous sample of polypeptides as described herein. However, the antigen may also be linked to a carrier protein such as keyhole limpet hemocyanin, particularly when the antigen is small. The immunization is typically accomplished by administering the sample to an immunologically competent mammal in an immunologically effective amount, i.e., an amount sufficient to produce an immune response. Preferably, the mammal is a rodent such as a rabbit, rat or mouse. The mammal is then maintained for a time period sufficient for the mammal to produce cells secreting antibody molecules that immunoreact with the receptor.

(b) A suspension of antibody-producing cells removed from the immunized mammal is then prepared. This is typically accomplished by removing the spleen of the mammal and mechanically separating the individual spleen cells in a physiologically tolerable medium using methods well known in the art.

(c) The suspended antibody-producing cells are treated with a transforming agent capable of producing a transformed ("immortalized") cell line. Transforming agents and their use to produce immortalized cell lines are well known in the art and include DNA viruses such as Epstein Bar Virus (EBV), Simian Virus 40 (SV40), Polyoma Virus and the like, RNA viruses such as Moloney Murine Leukemia Virus (Mo-MuLV), Rous Sarcoma Virus and the like, myeloma cells such as P3X63-Ag8.653, Sp2/O-Ag14 and the like.

In preferred embodiments, treatment with the transforming agent results in the production of an "immortalized" hybridoma by means of fusing the suspended spleen cells with mouse myeloma cells from a suitable cell line, e.g., SP-2, by the use of a suitable fusion promoter. The preferred ratio is about five spleen cells per myeloma cell in a suspension containing about $10^8$ splenocytes. A preferred fusion promoter is polyethylene glycol having an average molecule weight from about 1000 to about 4000 (commercially available as PEG 1000, etc.); however, other fusion promoters known in the art maybe employed.

The cell line is preferably of the so-called "drug resistant" type, so that unfused myeloma cells will not survive in a selective medium, while hybrids will survive. The most common class is 8-azaguanine resistant cell lines, which lack the enzyme hypoxanthine-guanine phosphoribosyl transferase and hence will not be supported by HAT (hypoxanthine, aminopterin, and thymidine) medium. It is also generally preferred that the myeloma cell line used be of the so-called "non-secreting" type which does not itself produce any antibody. In certain cases, however, secreting myeloma lines may be preferred.

(d) The transformed cells are then cloned, preferably to monoclonality. The cloning is preferably performed in a tissue culture medium that will not sustain (support) non-transformed cells. When the transformed cells are hybridomas, this is typically performed by diluting and culturing in separate containers the mixture of unfused spleen cells, unfused myeloma cells, and fused cells (hybridomas) in a selective medium which will not sustain the unfused myeloma cells. The cells are cultured in this medium for a time sufficient to allow death of the unfused cells (about one week). The dilution can be a limiting dilution, in which the volume of diluent is statistically calculated to isolate a certain number of cells (e.g., 1–4) in each separate container (e.g., each well of a microtiter plate). The medium is one (e.g., HAT medium) that will not sustain the drug-resistant (e.g., 8-azaguanine resistant) unfused myeloma cell line.

(e) The tissue culture medium of the cloned transformants is analyzed (immunologically assayed) to detect the presence of antibody molecules that preferentially react with Fn and with a Fn polypeptide or fusion protein of this invention. This is accomplished using well known immunological techniques. Thereafter, the antibody is screened for the ability to inhibit fibronectin binding to GPIIb-IIIa as described herein to identify those transformants producing antibody molecules that inhibit fibronectin binding to GPIIb-IIIa, i.e., inhibitory antibody molecules.

(f) A desired transformant is then selected and grown in an appropriate tissue culture medium for a suitable length of time, followed by recovery (harvesting) of the desired antibody from the culture supernatant by well known techniques. The suitable medium and suitable length of culturing time are also well known or are readily determined.

To produce a much greater concentration of slightly less pure monoclonal antibody, the desired hybridoma can be transferred by injection into mice, preferably syngeneic or semisyngeneic mice. The hybridoma will cause formation of antibody-producing tumors after a suitable incubation time, which will result in a high concentration of the desired antibody (about 5–20 mg/ml) in the bloodstream and peritoneal exudate (ascites) of the host mouse.

Media and animals useful for the preparation of these compositions are both well known in the art and commercially available and include synthetic culture media, inbred mice and the like. An exemplary synthetic medium is Dulbecco's minimal essential medium [DMEM; Dulbecco et al., *Virol.*, 8:396 (1959)] supplemented with 4.5 gm/l glucose, 20 mM glutamine, and 20% fetal calf serum. An exemplary inbred mouse strain is the Balb/c.

The monoclonal antibodies produced by the above method can be used, for example, in diagnostic and therapeutic modalities wherein formation of a Fn-containing immunoreaction product is desired. Methods for producing hybridomas that generate (secrete) antibody molecules having a desired immunospecificity, i.e., having the ability to immunoreact with a particular protein, an identifiable epitope on a particular protein and/or a polypeptide, but not immunoreact with a second polypeptide, such as the Eighth Type III repeat, are well known in the art and are described further herein. Particularly applicable is the hybridoma technology described by Niman et al., *Proc. Natl. Acad. Sci. USA*, 80:4949–4953 (1983), and by Galfre et al., *Meth. Enzymol.*, 73:3–46 (1981), which descriptions are incorporated herein by reference.

A further preferred method for forming the instant antibody compositions involves the generation of libraries of Fab molecules using the method of Huse et al., *Science*, 246:1275 (1989). In this method, mRNA molecules for heavy and light antibody chains are isolated from the immunized animal. The mRNAs are amplified using polymerase chain reaction (PCR) techniques. The nucleic acids are then randomly cloned into lambda phages to generate a library of recombined phage particles. The phages can then be used to infect an expression host such as *E. coli*. The *E. coli* colonies and corresponding phage recombinants can then be screened for those producing the desired Fab fragments.

The antibody molecule-containing compositions employed in the present invention can take the form of solutions or suspensions. The preparation of a composition that contains antibody molecules as active ingredients is well understood in the art. Typically, such compositions are prepared as liquid solutions or suspensions, however, solid forms suitable for solution in, or suspension in, liquid can also be prepared. The preparation can also be emulsified. The active therapeutic ingredient is often mixed with excipients which do not interfere with the assay and are compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents, and the like, which enhance the effectiveness of the active ingredient.

An antibody molecule composition can be formulated into a neutralized acceptable salt form. Acceptable salts include the acid addition salts that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Examples

The following examples are presented only for purposes of illustration and in no way limit the invention.

1. Isolation of GPIIb-IIIa

The following procedure allows large scale preparation of platelet membrane GPIIb-IIIa protein from lysed platelets, and is essentially as described by Charo et al, *J. Biol. Chem.*, 266:1415–1421 (1991).

| Reagents: | | Final concentration |
|---|---|---|
| Modified Tyrode's Buffer: | | |
| 50 ml | 10x Tyrode's buffer | 1x |
| 0.5 g | crystalline BSA (Sigma cat. #A-4378) | 1 mg/ml |
| 0.5 g | dextrose (d-glucose) | 1 mg/ml |
| 0.58 g | HEPES | 10 mM |
| 0.5 ml | 1 M CaCl$_2$ | 1 mM |
| 2.5 ml | 200 mM MgCl$_2$ | 1 mM |
| bring to 500 ml with H$_2$O, and pH to 6.5 with HCl | | |
| 10X Tyrode's Buffer: | | |
| 160 g | NaCl | 1.5 M |
| 20.3 g | NaHCO$_3$ | |
| 3.9 g | KCl | |
| Dissolve in 2 liters of double distilled H$_2$O | | |
| Lysis Buffer: | | |
| 0.348 g | HEPES | 10 mM |
| 4.8 g | NaCl | 0.15 mM |
| 4.42 g | Beta-Octylglucoside | 50 mM |
| 0.3 ml | 1 M CaCl$_2$ | 1 mM |
| 2 ml | 200 mM MgCl$_2$ | 1 mM |
| 2 ml | 150 mM PMSF in EtOH | 1 mM |
| 60 ul | 50 mM leupeptin | 10 mM |
| 0.3 g | NEM (N-ethylmaleimide) | 1 mg/ml |
| Bring to 300 ml volume with H$_2$O. Adjust pH to 7.4. | | |

Platelet packs from a blood bank are transferred to disposable 50 ml conical tubes (Falcon), balance and spun in Sorvall RT-6000 at 800 rpm (xg) for 10 minutes at 22° C. to pellet RBCs. Supernatants are transferred to clean 50 ml conical tubes and spun at 2300 rpm for 20 minutes at 22° C. The supernatant is transferred to autoclavable bottle for disposal. Using a plastic 25 ml pipet and Modified Tyrode's Buffer, the platelet pellets are resuspended in one-half of the original volume and spun again at 2300 rpm for 20 minutes at 22° C. The pellets are resuspended in Modified Tyrode's Buffer as before and spun again at 2300 rpm for 20 minutes at 22° C. The platelet pellet is resuspended in Lysis buffer (2 ml/platelet pack), spun in ultracentrifuge (SW 41 centrifuge rotor) for 20 minutes at 20,000 rpm at 4° C., and the supernatant is collected and stored frozen. Caution: The platelets should not be allowed to come in contact with glass and should always be kept at room temperature to avoid aggregation.

GPIIb-IIIa from platelet lysates is purified by the following procedure:

| Reagents RGD-Affinity chromatography column Buffer: | | |
|---|---|---|
| 0.348 g | HEPES | 10 mM |
| 4.8 g | NaCl | 0.15 M |
| 2.2 g | Beta-Octylglucoside | 25 mM |
| 0.3 ml | 1 M CaCl$_2$ | 1 mM |
| 1.5 ml | 200 mM MgCl$_2$ | 1 mM |
| 2 ml | 150 mM PMSF in EtOH | 1 mM |
| 60 ul | 50 mM leupeptin | 10 uM |
| 0.3 g | NEM (N-ethylmaleimide) | 1 mg/ml |
| Bring volume to just under 300 ml with H$_2$O, pH to 7.4, then adjust volume to 300 ml. Or use HEPES/NaCl Pre-made | | |

F7F-Sepharose Columns: F7F-Sepharose: KYGRGDS-Sepharose (SEQ ID NO 3), 10 mg KYGRGDS/ml CNBr-activated Sepharose. 1 ml of F7F-Sepharose is loaded per column in 7 ml disposable columns from Evergreen Scientific.

The following chromatographic procedure was employed: 8.1 ml columns of F7F-Sepharose was equilibrated with 10 mls Lysis Buffer per column. The columns were allowed to drain until surface of F7F-Sepharose is just exposed, then 1 ml of Platelet Lysate (1 ml Platelet Lysate - 1 platelet pack) was applied.

The column was drained until the yellow color of the Platelet Lysate just reaches the bottom of the column, cap both ends of the column and invert overnight at 4° C. and the flowthrough was collected. The columns were washed with 10 mls each of Column Buffer and the washes were collected. The column was eluted with 2 mls per column of 1 mg/ml GRGDSP (2:330–335) in Column Buffer followed by 2 mls of Column Buffer. One ml fractions were collected and pooled to form purified GPIIb-IIIa. The concentration of purified GPIIb-IIIa collected was determined by its absorbance at 280 nm.

2. Preparation of Monoclonal Antibody Compositions

Monoclonal antibodies that immunoreact with a receptor binding site on fibronectin were produced using standard hybridoma technology with exceptions as noted. Briefly, two Balb/c mice were each immunized intraperitoneally four times at one week intervals with increasing doses (1 mg, 10 mg, 25 mg, 50 mg and 100 mg, respectively) of immunogen consisting of a mixture comprised of affinity-isolated GPIIb-IIIa, as prepared in Example 1 (1.25 mg/ml) and fibronectin (Fn) at 3 mg/ml. The immunogen was diluted 1:1 in Complete Freund's Adjuvant for the first immunization, in Incomplete Freund's Adjuvant for the second and third immunization, and in normal saline for the fourth. Three days after the fourth immunization about $1 \times 10^8$ lymphocytes were isolated from the spleens of both mice, admixed into a suspension and fused with $5 \times 10^7$ P3X63AG8.053 mouse myeloma cells using 50% PEG 1500 as the cell fusion promoter. The resulting transformed (fused) antibody-producing cells (hybridomas) were initially transferred to 96-well microtiter plates at a density of about $1 \times 10^6$ cells per well and cultured in selective HAT media.

Fibronectin (Fn) was purified as described by Plow et al, *J. Biol. Chem.*, 256:9477–9482 (1981) and U.S. Pat. No. 4,589,981. Briefly, Fn was isolated from fresh human citrated plasma by affinity chromatography on gelatin-sepharose as described by Engvall et al., *Int. J. Cancer*, 20:1–5 (1977). Bound Fn was eluted with 1M sodium borate at pH 5.3 and the major eluted protein peak was dialyzed against 0.15M NaCl, 0.01M sodium phosphate of pH 7.0. The isolated Fn yielded a single band on SDS-PAGE under nonreducing conditions and a closely spaced doublet of 215,000 to 230,000 molecular weight under reducing conditions.

Tissue culture supernatants from about 2000 wells appearing to contain viable HAT resistant hybridoma cells after 8 days of culturing were screened in the ELISA assay for the presence of antibody molecules that immunoreact with fibronectin. The isolated hybridomas were then subcloned twice at limiting dilutions to provide about 1 cell per well and 24 of the resultant hybridoma cultures were shown to be of monoclonal origin on the basis of two criteria: (1) each supernatant was from a single cell foci and immunoreacted with fibronectin in the ELISA screen, (2) each supernatant contained a single isotype of immunoglobulin when analyzed using the Mouse Ig Screening and Isotyping Kit according to the instructions provided by the manufacturer, Boehringer-Mannheim Biochemicals, Indianapolis, Ind.

The positive supernatants immunoreactive with fibronectin were screened for their ability to inhibit binding of $^{225}$I-fibronectin to GPIIb-IIIa coated microtiter cells as described in Example 4. Positive supernatants were screened in this way at each subcloning of hybridomas. The monoclonal antibody molecules were prepared by isolating the antibody molecules from the ascites fluid of a mouse using protein A-Sepharose typically obtained from Pharmacia Inc. (Piscataway, N.J.) and used according to manufacturer's instructions. The protein concentration of isolated antibody molecule compositions as needed was determined using the Bio-Rad Protein Assay Kit (Bio-Rad, Richmond, Calif.) according to the manufacturer's instructions.

To prepare a monoclonal antibody composition containing $^{125}$I-lapeled antibody molecules, 350 microliters (µl) of PBS (0.15M NaCl, 0.01M sodium phosphate, pH 7.09) containing 1 milligram per milliliter (mg/ml) of the above isolated antibody molecules were admixed with 40 micrograms (µg) of chloramine-T and 1 millicurie (mCi) of carrier-free Na$^{125}$I (Amersham, Arlington Heights, Ill.). The resulting admixture was maintained for 5 minutes at about 20° C. and then admixed with 20 µl of a 2 mg/ml sodium metabisulfite solution (2 mg/ml) and 20 µl of a potassium iodide solution. Thereafter, 800 µl of PBS containing 1% BSA were admixed followed by further admixture of diisopropylfluorophosphate to a final concentration of 10 mM. The resulting admixture was maintained for 60 minutes at 22° C. and then dialyzed against PBS. The specific activity of the resulting $^{125}$I-labeled antibody molecules was about 4.5 microCurie (uCi) per ug.

Compositions containing Fab fragments from the above isolated antibody molecules were prepared by digestion with papain (200:1 weight per weight of Ig to papain) for 6 hours at 37° C. following the methods of Mage et al., *Methods in Enzymology*, 70:142–150 (1980). Undigested Ig and Fc fragments were removed by chromatography on protein A-Sepharose. The resulting Fab fragments-containing compositions were then ready for use, or were $^{125}$I-labeled, as needed, using the same procedures as described above for monoclonal antibody compositions.

3. ELISA Assays a. ELISA To Screen Monoclonal Antibodies

Antibody molecules contained in hybridoma culture supernatants were examined for their ability to immunoreact with fibronectin. Fifty microliters (µl) of coating solution (0.1M NaHCO$_3$, pH 8.0, 0.1% NAN$_3$) containing 10 mg/ml of isolated fibronectin prepared as in Example 2 were admixed into the wells of flat-bottom 96-well microtiter plates (Immulon 2; Dynatech Laboratories, Chantilly, Va.). The plates were then maintained for 60 minutes at 37° C. to permit the fibronectin to adsorb onto the walls of the wells. The coating solution was removed by shaking, the wells were rinsed twice with washing buffer (10 mM Tris-HCl at pH 7.4, 0.05% (v/v) TWEEN-20, 0.15M NaCl, and 200 mg/ml merthiolate), and 200 µl of blocking solution (5% bovine serum albumin (BSA;w/v) in coating solution) were admixed into each well (solid support) to block excess protein sites.

The wells were maintained for 60 minutes at about 37° C. and then the blocking solution was removed. About 50 µl of hybridoma culture supernatant diluted 1:1 in dilution buffer consisting of 0.1% (w/v) BSA in washing buffer was added to each well to form an immunoreaction admixture. The resulting solid/liquid phase immunoreaction admixtures were maintained at room temperature for 60 minutes to permit formation of a first solid phase-bound fibronectin-ligand complex and admixed antibodies. The solid and liquid phases were then separated, the wells were rinsed twice with washing buffer, and excess liquid was removed by shaking.

Fifty μl of a solution containing horseradish peroxidase labeled goat anti-mouse IgG (Tago Inc., Burlingame, Calif.) diluted 1:1000 in dilution buffer was admixed into each well to form a second solid liquid phase immunoreaction admixture (labeling immunoreaction admixture). The wells were maintained for 60 minutes at room temperature to permit formation of a second immunoreaction product between the labeled antibody and any solid phase-bound antibody of the first immunoreaction product and then rinsed twice with washing buffer to isolate the solid phase-bound label-containing immunoreaction products. Excess liquid was then removed from the wells.

Fifty μl of freshly prepared chromogenic substrate solution containing 4.0 mg/ml 0-phenylenediamine and 0.012% (v/v) hydrogen peroxide in CP buffer (243 μl of 0.1 m citric acid and 250 μl of 0.2M dibasic sodium phosphate per liter $H_2O$, pH 5.0) were then admixed into each well to form a color developing-reaction admixture. After maintaining the color developing-reaction admixture for 10 minutes at about 20° C., 50 μl of 2N $H_2SO_4$ were admixed into each well to stop the developing-reaction, and the resulting solutions were assayed for absorbance at 490 nanometers (nm) light wavelength using a Model 310 ELISA plate reader (Bio-Tek Instruments, Winooski, Vt).

Antibody molecule compositions were considered to contain anti-fibronectin immunoreactive antibody molecules if the measured absorbance at 490 nm (A490) was at least 6 times above background i.e., above about 0.3 optical density units when measured at A490. A panel of monoclonal antibodies (MAbs) immunoreactive with fibronectin were identified, including the MAbs FnI-8, Fn-11 and FnI-16, described further herein.

4. Screening Mab Inhibition of Fn-GPIIb-IIIa Interaction

The following microtiter well assay for binding of $^{125}$I-labeled fibronectin to GPIIb-IIIa was used:

Removable microtiter wells were coated with RGDS-affinity purified GPIIb-IIIa (purified in Example 1 and using 50 μl per well at >10 mg/ml) at 4° C. overnight. The wells were blocked by dumping out the GPIIb-IIIa and incubating the wells in 150 μl 5% BSA for 1–2 hrs. at room temperature. 25 μl of 25 nM $^{125}$I-labeled fibronectin (final concentration in well 12.5 nM) in 2× Modified Tyrodes was pre-incubated with 25 μl of hybridoma culture supernatant diluted 1:1 in 10 mM Tris-HCl (pH 8) for 30 minutes at 37° C. in a separate microtiter welltray. Fibronectin prepared as in Example 2 was iodinated with $^{125}$I using the Chloramine T method described by Plow et al, *J. Biol. Chem.*, 256:9477–9482 (1981). The GPIIb-IIIa coated and blocked microtiter wells were washed 4 times with Modified Tyrodes Buffer. The $^{125}$I-fibronectin supernatant solution was transferred to the GPIIb-IIIa coated wells and incubated at room temperature for 4 hrs. The wells were washed 4 times with 200 μl Modified Tyrodes. The empty wells were counted in a gamma counter and cpm/well determined.

Results are shown as an average (± one standard deviation) of triplicate measurements, and expressed as a percent fibronectin (Fn) bound relative to the amount of Fn bound in the absence of added antibody. Three MAbs out of a panel of 2000 Fn-immunoreactive MAbs were identified that inhibited Fn binding to GPIIb-IIIa by this assay, and were designated FnI-8, FnI-11 and FnI-16. All three MAbs were identified as being of the $IgG_1$ isotype using the Mouse Ig Screening and Isotyping Kit (Boehringer Mannheim, Indianapolis, Ind).

In similar inhibition assays as described above, the three MAbs were shown to inhibit binding of 50 nanomolar (nM) Fn to GPIIb-IIIa with an $IC_{50}$ of 100 to 175 nM.

The inhibitory Mabs FnI-8, FnI-11 and FnI-16 were screened in a cross-competition ELISA assay for binding to fibronectin to determine whether they were immunoreactive with different epitopes on fibronectin. In that assay, fibronectin was coated to the wells of the microtiter plate at 10 ug/ml as above rather than GPIIb-IIIa. After blocking, 1 ug/ml of $^{125}$I labelled MAb was incubated for 2 hours at room temperature in the presence of 50 ug/ml of unlabelled competing MAb. After washing, the amount of bound radioactivity was determined. Results for an average (± one standard deviation) of three determinations are shown in FIG. 1A. MAbs FnI-11 and FnI-16 competed with each other for binding to Fn. In contrast, there was no competition between FnI-8 and FnI-11, and FnI-8 and FnI-16 were only minimally cross-inhibitory. Thus, the epitopes for FnI-8 and FnI-11 are distinct, and the epitope for FnI-11 and FnI-16 are related.

A competitive ELISA similar to the above ELISA was conducted on the three inhibitory MAbs to determine the ability of the anti-Fn MAbs to immunoreact with human Fn in the presence of plasma Fn from various non-human species. In that assay, plasma was added to an immunoreaction mixture containing a MAb in a microtiter well coated with Fn as above. The presence of MAb immunoreacted with Fn is detected a secondary peroxidase-labelled anti-mouse antibody in the presence of the chromogenic substrate o-phenylenediamine. The binding of FnI-8 to human Fn was inhibited by human, bovine and guinea pig plasma, whereas FnI-11 and FnI-16 were inhibited only by human plasma. Thus the epitope identified by FnI-8 is particularly useful in that it is present on multiple species of Fn.

5. Preparation and Isolation of Fn Fragment-MBP Fusion Proteins

Two MBP encoding plasmids, pPR734 and pIH821, were employed as vectors for expressing the instant GPIIIa-MBP fusion proteins in *E. coli*. The MBP region of the fused protein allows ready purification of the fused product from other cellular proteins. The vectors were constructed via well-known techniques (Sambrook et al, in "Molecular Cloning: A Laboratory Manual", Cold Spring Harbor Laboratory Press, Cold Spring Harbor, N.Y.) following the procedures described hereinbelow.

A. Construction of MBP Vector

A cDNA clone containing the complete sequence of fibronectin (Fn) is described by Obara et al, *Cell*, 53:649–657 (1988), and was provided by Dr. Yamada, an author on the publication. The provided cDNA clone was subjected to restriction endonuclease digestion with PvuII, and the resulting digested fragments were blunt-end ligated with EcoRI linkers to adapt the digested fragments to contain EcoRI termini. The adapted fragments were then digested with PstI to cleave those fragments susceptible to PstI (thereby inactivating the PstI-cleaved fragments for ligation into an EcoRI site). The maltose binding fusion protein vector pIH821 (New England Biolabs, Inc., Beverly, Mass.) and the adapted fragments were both digested with EcoRI to produce EcoRI cohesive termini, and the Fn fragment was ligated into the vector using DNA T4 ligase to form a fusion construct having the cloned Fn-coding gene fragment operatively linked to MBP-coding gene fragment capable of expressing a Fn-MBP fusion protein. The PvuII fragment contains the region of Fn corresponding to residues 1235–1436. This plasmid construct is designated pIHPBam and expresses the MBP fusion protein designated MBP/8–9 or MBP-Fn(1235–1436).

Figure 2:
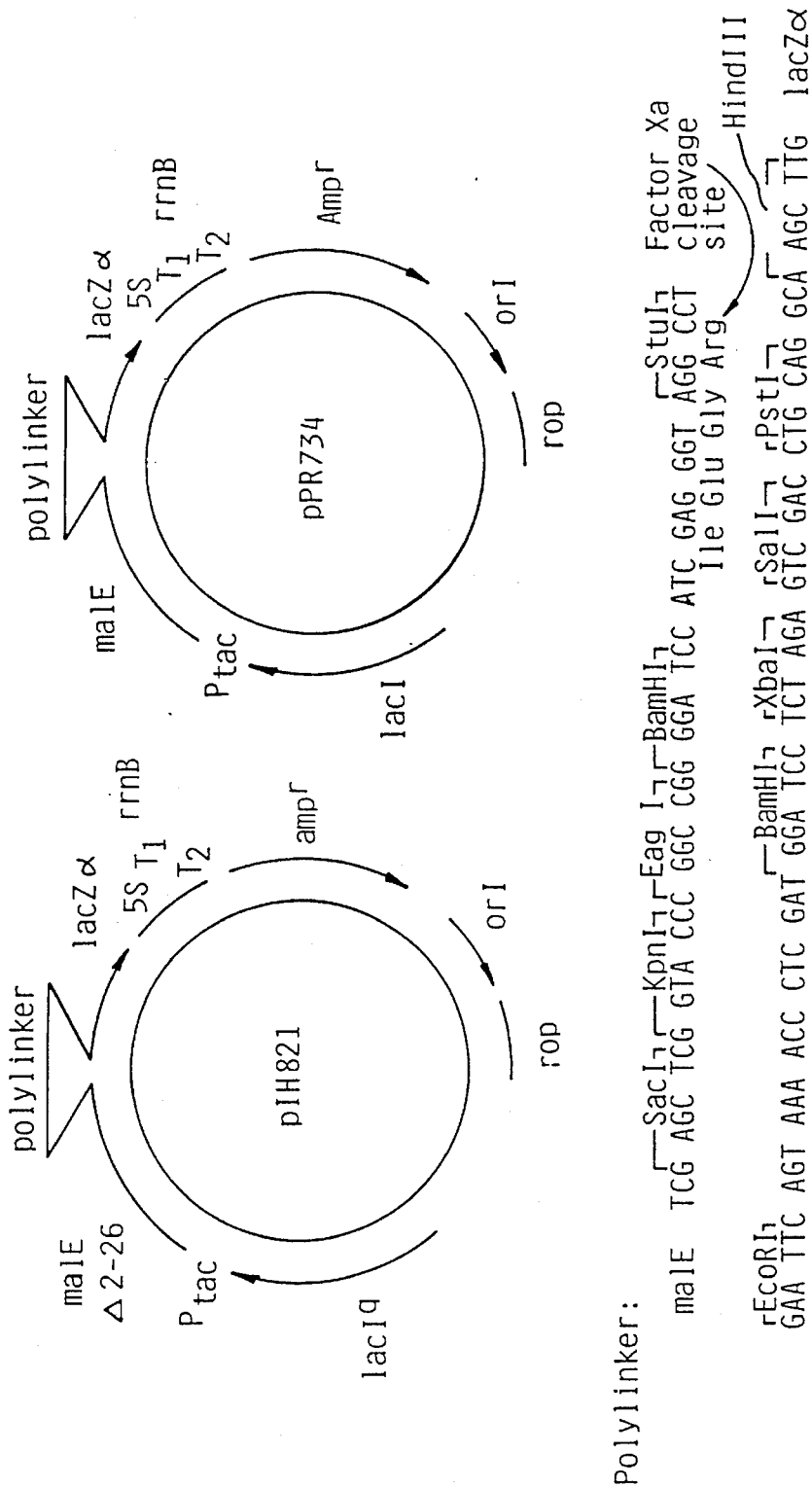
FIG. 2 shows MBP vectors pIH821 and pPR734 for synthesizing GPIIIa-MBP fusion proteins, and relevant cloning sites.

Vectors pIH821 and pPR734 are depicted in FIG. 2, and were obtained from New England Biolabs (Beverly, Mass.).

The vectors each have a malE linked via a polylinker to a lacZ gene. pIH821 is identical to pPR734 except that PIH821 has a deletion of the malE signal sequence 2–26, which facilitates export of fusion protein to the periplasm. The vectors each have a tac promoter (Ptac) upstream of the malE gene. A lac I$^Q$ suppressor gene immediately upstream of the tac promoter allows suppression of expression activity until IPTG (isopropyl β-D-thiogalactoside) is used to induce expression. The remaining vector backbone is from AvaI (filled in) to Eco R1 (filled in) of pKK233-2 (Pharmacia, Piscataway, N.J.).

The important components of the maltose-binding protein fusion expression system (MBP expression system) are the promoter (PtacII) previously described by Amann et al., Gene, 25:167–178 (1983); the maltose binding protein-lacZα and fusion gene (malE-LacZα) previously described by Guan et al., Gene, 67:21–30 (1987); the rrn B ribosomal transcription terminator previously described by Brosius et al., Proc. Natl. Acad. Sci. USA, 81:6929–6933 (1984) and commercially available in the pIH821 and pPR734 vectors (New England Biolabs, Beverly, Mass.) and in the pKK223-3 and pKK233-2 (Pharmacia, Piscataway, N.J.). The MBP expression system optionally contains the gene coding for the lac repressor gene (lac I) previously described by Farabaugh, Nature, 274:765–769 (1978). If the lac I gene is not present on the expression vector it may be provided in trans by using the bacterial strains expressing the lambda repressor such as JM101, JM105, JM107, JM109 (ATCC #33323) and JM110 (ATCC #47013) described by Yanisch-Perron et al., Gene, 33:103 (1985) which are commercially available from Stratagene (La Jolla, Calif.).

The individual nucleic acid segments containing the components of this expression system are operatively linked together (ligated) using standard molecular biology techniques, such as those described in *Molecular Cloning: A Laboratory Manual, Second Edition*, Sambrook et al., eds, Cold Spring Harbor Laboratories, N.Y. (1989). When necessary, the reading frame of the various components is adjusted using synthetic linkers, various fill-in reactions or various exonucleoses. In addition, various deletions and adjustments in the reading frame are easily made using loop-out mutagenesis and the commercially available mutagenesis kits such as the mutagene kit from Bio Rad Laboratories (Richmond, Calif.).

Each of the required components of the expression system will now be described in detail. The Ptac II promoter previously described by Amann et al., Gene, 25:167–178 (1983) may be isolated from a number of available vectors, such as PKK-223-3 (Pharmacia), PIH821 and pPR734 (New England BioLabs, Beverly, Mass.), Ptac II (ATCC #37245) and Ptac 12 (ATCC #37138) described by Amann et al., Gene, 25:167–178 (1983). For example, the Ptac II promoter may be isolated using restriction endonucleases from Ptac II using Eco RI and Hind III or ClaI and Hind III.

The maltose binding protein-lacZα fusion gene (malE-lacZα) previously described by Guan et al., Gene, 67:21–30 (1987) contains the malE gene on a Hinf I restriction endonuclease fragment isolated from the chromosome of an E. coli such as HB101 (ATCC #33694) or wild type E. coli K12. The malE gene has been sequenced by Duplay et al., J. Biol. Chem., 259:10606–10613 (1984) and therefore probes specific for the malE gene may be easily synthesized allowing the malE gene to be isolated from E. coli using standard cloning protocols. Alternatively, the malE gene may be chemically synthesized in segments and these segments joined using T4 DNA Ligase to produce the malE gene. The mature maltose binding protein (the malE gene product) is coded for by codons 28–342 of the malE gene sequence as described by Duplay et al., J. Biol. Chem., 259:10606–10613 (1984). The expression vector may either contain the entire malE gene coding for the 27 amino acid maltose binding protein leader sequence and codons 28 to 392 coding for the mature maltose binding protein or only the portion of the malE gene coding for the mature maltose binding protein.

The remainder of the maltose binding protein-lacZα fusion gene contains the portion of the lacZ gene coding for the shorter alpha (α) peptide of the lac gene (approximately 107 amino acids in length). This lacZ gene may be isolated from pUC 19 described by Yanisch-Perron et al., Gene, 33:103–119 (1985) and is commercially available. The lacZ gene and the malE gene are linked together using a linker that may optionally have various useful restriction endonuclease recognition sequences in it.

The rrn B ribosomal transcription terminator previously described by Brosius et al., Proc. Natl. Acad. Sci. USA, 81:6929 (1984) and Brosius et al., Plasmid, 6:112–118 (1981). The rrn B ribosomal transcription terminators may be easily isolated from available vectors, such as PEA300 (ATCC #37181), PKK 223-3 and PKK 233-2 (Pharmacia), and PIH821 and PPR734 (New England Biolabs). For example, the rrn B ribosomal transcription terminator may be isolated from pKK223-3 using Hind III and Pvu I restriction endonucleases.

The lacI gene coding for the lambda repressor protein has been sequenced by Farabaugh, Nature, 274:765 (1978). In addition, the lacI gene is in several available vectors, such as pBluescript II KS and pBluescript SK (Stratagene); and pUC 18 and pUC 19 (Pharmacia). The lacI gene may be isolated from these vectors using restriction endonucleases and standard molecular biology techniques. The lacI gene may be present in the expression vector or present in the bacteria the expression vector is grown in.

The multiple cloning site present in the expression vector between the malE and lacZ genes is shown in Table 1 and listed in the Sequence Listing as

TABLE 1

Sequence of Polylinker in Expression System

| | Sac I | | Kpn I | | Eag I | | BamH I | | | |
|---|---|---|---|---|---|---|---|---|---|---|
| malE | TCG | AGC | TCG | GTA | CCC | GGC | CGG | GGA | TCC | ATC | GAG |

| | | Stu I | | Eco RI | | | | | |
|---|---|---|---|---|---|---|---|---|---|
| GGT | AGG | CCT | GAA | TTC | AGT | AAA | ACC | CTC | GAT |
| | | | | Factor X cleavage site | | | | | |

| | BamH I | | Xba I | | Sal I | | Pst I | | Hind III | |
|---|---|---|---|---|---|---|---|---|---|---|
| GGA | TCC | TCT | AGA | GTC | GAC | CTG | CAG | GCA | AGC | TTG | lacZα |

TABLE 1-continued

Sequence of Polylinker in Expression System

Deletion of the malE Signal Sequence (FIG. 2):

malE start codon
ATG(D2–26)AAA ATC malE...
deletion of codons 2–26(signal sequence)

The multiple cloning site (polylinker) contains a nucleic acid segment that codes for a factor Xa cleavage site located between the malE and lacZ genes. Any maltose binding protein fusion protein produced by this vector may be cleaved at the factor Xa cleavage site thereby facilitating the purification of the desired protein.

Foreign genes may be inserted (operatively linked) into the multiple cloning sequence at the Sac I, Kpn I, Eag I or Bam HI restriction endonuclease sites.

A Fn(1235–1436)-MBP fusion protein encoding plasmid expressing the 1235–1436 (2:73–274) region of Fn in a MBP fusion protein was prepared as described above.

The EcoRI fragment described above that contains the 1235–1436 fragment was inserted into a plamsid at its EcoRI site to form phfnP. Subsequently, plasmid phfnP was digested with BamHI, the ends were filled, an XbaI polylinker was ligated to the filled (blunt) ends, the ligated plasmid was digested with SalI to produce a XbaI-SalI fragment containing the Fn region 1359–1436 (2:217–274), and the Fn fragment was inserted into pIH821 to form plasmid pPIHBam that expressed Fn(1359–1436)-MBP fusion protein.

Fn cDNA fragments cloned in frame with the lacZ gene of lambda gt11 have been previously described by Obara et al, Cell, 53:649–657 (1988). These clones express a Fn-lacZ fusion protein, and include the Fn fragments spanning Fn residues 934–1653, 1317–1653 (2:155–491) and 1359–1653 (2:197–491).

A 603 base pair (bp) PvuII fragment was isolated from the lambda gt11 clone fn' provided and described by Obara et al, supra, which fragment has the internal EcoRI cleavage site eliminated, and the fragment inserted into the EcoRI site of lambda gt11 using an EcoRI polylinker using standard techniques. The construct expressed Fn residues 1235–1436 (2:73–274) fused to β-galactosidase, designated Fn(1235–1436)Bgal.

A 651 bp fragment from an EcoRI digest of lambda gt11 D(934–1163)fn from Obara et al, supra, was inserted into lambda gt11 to generate the construct which expressed Fn residues 1163–1379 (2:1–217), designated Fn(1163–1379)-Bgal. 1A clone which expressed Fn residues 1380–1653 (2:218–491) in frame with the lacZ gene product was constructed by inserting a 757 bp EcoRI fragment from lambda gt11 D(934–1163)fn into the EcoRI site of lambda ZAP II vector (Stratagene, La Jolla, Calif.), the expressed product designated as Fn(1380–1653)-Bgal.

B. Expression of a MBP-Fusion Protein

A small scale experiment is described to determine the behavior of a particular MBP fusion protein. This protocol results in three crude extract fractions; a total cell crude extract, a suspension of the insoluble material from the crude extract, and a periplasmic fraction prepared by the cold osmotic shock procedure. Inoculate 80 ml rich broth+glucose & amp (per liter, 10 g Tryptone, 5 g yeast extract, 5 g NaCl, 1 g glucose, autoclave, add ampicillin to 100 µg/l) with cells containing the fusion plasmid produced above designated MBP/8–9. Grow at 37° C. with good aeration to $2 \times 10^8$ cells/ml. Take a sample of 1 ml and centrifuge for two minutes in a microfuge (uninduced cells). Discard supernatant and resuspend the cells in 100 µl SDS-PAGE sample buffer. Vortex and place on ice.

Add IPTG (isopropylthiogalactoside) to the remaining culture to give a final concentration of 0.3 mM, e.g., 0.24 ml of a 0.1M stock in $H_2O$. Continue incubation at 37° C. for 2 hours. Take a 1 ml sample and centrifuge for 2 minutes in a microfuge (induce cells). Discard supernatant and resuspend the cells in 150 µl SDS-PAGE sample buffer. Vortex to resuspend cells and place on ice. (Additional time points at 1 and 3 hours can be helpful in trying to decide when to harvest the cells for a large scale prep.)

Divide the culture into two aliquots and harvest the cells by centrifugation at 4000×g for 10 minutes. Discard the supernatant and resuspend one pellet (sample A) in 5 ml 10 mM sodium phosphate, 30 mM NaCl, 0.25% Tween 20, 10 mM EDTA, 10 mM EGTA (Sigma E 4378), pH 7.0. Resuspend the other pellet (sample B) in 10 ml 30 mM Tris-HCl, 20% sucrose, pH 8.0 (9 ml for each 0.1 g cells wet weight). (The buffers specified contain sodium phosphate, pH 7.0. The original buffers used in the MBP affinity purification used Tris-HCl pH 7.2. However, Tris is a very poor buffer at pH 7.2, making it difficult to get predictable buffers by dilution of concentrated stock solutions. Both buffers give excellent results, and other neutral buffers probably would work as well).

Freeze Sample A in a dry ice-ethanol bath (or overnight at 20° C.) then thaw in cold water. Sonicate the sample and monitor cell breakage by measuring the release of protein using the Bradford assay or $A_{280}$, until it reaches a maximum. Centrifuge at 9,000×G for 20 minutes. Decant the supernatant (crude extract 1) and save on ice. Resuspend the pellet in 5 ml 10 mM sodium phosphate, 0.25% Tween 20, 30 mM NaCl, 10 mM EDTA, 10 mM EGTA, pH 7.0. This is a suspension of the insoluble matter (crude extract 2). The reason for preparing three different extracts in this pilot experiment is to see the fusion 1) forms insoluble inclusion bodies, or 2) is exported to the periplasmic space. If the fusion protein in insoluble, the protocol must be modified to produce soluble protein (see below). If the fusion is efficiently exported, preparation of a periplasmic fraction should be considered as an alternative to preparing a crude cellular extract. Preparation of a periplasmic extract gives a substantial purification by itself.

Add EDTA to 1 mM of Sample B and incubate for 5–10 minutes at room temperature with shaking or stirring. Centrifuge at 4° C., remove all the supernatant, and resuspend the pellet in 10 ml ice-cold 5 mM $MgSO_4$. Shake or stir for 10 minutes in an ice bath. Centrifuge at 4° C. The supernatant is the cold osmotic shock fluid.

Add 5 µl 2X SDS-PAGE sample buffer to 5 µl of crude extracts 1 & 2 and 10 µl 2× SDS-PAGE sample buffer to 10 µl of the cold osmotic shock fluid. Boil these samples, along with the uninduced and induced cell samples, for 5 minutes.

Centrifuge in a microfuge for 2 minutes. Load 20 μl of the uninduced and induced cells samples, and all of the extract samples, on a 10% SDS-PAGE gel. Optionally, one can run an identical SDS-PAGE gel(s) using 1:5 dilutions of the above samples, prepare a Western blot and develop with anti-MBP serum and, if available, serum immunospecific for the cloned portion of the fusion protein. Another pilot to optimize export of the fusion protein, i.e. find the best temperature (23°, 30°, or 37° C.) and IPTG level, and the best time to harvest the cells, may be desirable. If the fusion protein is in insoluble matter, make sure that the cells are completely broken. If it is still insoluble, try extracting the pellet with 0.2% Triton X-100, 1 mM EDTA a few times; often the protein is not truly insoluble but just associated with the membrane fragments in the cell pellet. If this is the case, be aware that, for some fusions, Triton interferes with binding to the column. If the protein is truly insoluble, modify the conditions of cell growth to attempt to produce soluble fusion protein. Three changes that have helped in previous cases are i) changing to a different strain background, ii) growing the cells at 23° C. or 30° C., and iii) inducing with 0.01 mM IPTG to give lower expression levels (Takagi et al., *Biotechnology*, 6:948 (1988)).

C. Purification of MBP-Fusion Protein (1) Preparation of Cross-linked Amylose Resin For 300 ml resin, place 10 g. amylose (Sigma, Catalog No. A-7043), 40 ml $H_2O$ and a stirring bar in a 1000 ml beaker and warm to 50° C. with stirring. In a fume hood, add 60 ml 5N NaOH, then 30 ml epichlorhydrin (Sigma, Catalog No. E-4255) with rapid stirring. The suspension will heat up upon gelling. Continue stirring until the suspension forms a solid gel, about 10 minutes (it should turn a little yellow). Let cool to room temperature (about 45 minutes–1 hour) then cut the gel into pieces and wash three times with 1000 ml $H_2O$. Transfer the gel to a Waring blender and fragment the gel for about 3–5 s. Wash with 1000 ml 50 mM glycine-HCl, 0.5M NaCl, pH 2.0, two times and discharge the fines between washes.

Wash with water 3 times (keep discharging fines), then with 10 mM sodium phosphate, pH 7.0, three times. Suspend the gel in 10 mM sodium phosphate, 0.02% sodium azide, pH 7.0 and store at 4° C. Block non-specific sites on the resin by washing in 1000 ml 3% non-fat dry milk overnight at 4° C.

(2) Affinity Chromatography

The following are protocols for large scale purification of a MBP-fusion protein.

Inoculate 1 liter rich broth, glucose and ampicillin (per liter, 10 g Tryptone, 5 g yeast extract, 5 g NaCl, 1 g glucose, autoclave, add ampicillin to 100 μg/ml) with cells containing a plasmid that expresses a MBP fusion protein. Grow to $2\times10^8$ cells/ml ($A_{600}$ of .4). Add IPTG to a final concentration of 0.3 mM, e.g. 85 mg or 3 ml of a 0.1M stock in $H_2O$. Incubate the cells at 37° C. for 1–3 hours. (The period of time to allow for expression depends on the host used and whether the MBP-fusion protein is unstable, and should be determined empirically.) Harvest the cells by centrifugation at 4000×g and resuspend in 50 ml 10 mM sodium phosphate, 30 mM NaCl, 0.2% Tween 20, 10 mM β-mercaptoethanol, 10 mM EDTA, 10 mM EDTA, 10 mM EGTA (Sigma, Catalog No. E 4378), pH 7.0. Freeze the resuspended sample in a dry ice-ethanol bath (or overnight at 20° C.) and thaw in cold water. Sonicate and monitor cell breakage, by measuring the release of protein using the Bradford assay or $A_{280}$, until it reaches a maximum. Centrifuge at 9,000×g for 30 minutes and collect the supernate to form a crude extract. (For many unstable proteins, most of the degradation happens during harvest and cell breakage. Therefore, it is best to do it quickly and keep the cells chilled. Fifty ml of lysis buffer is based on the expectation of about 5 grams cells/liter, i.e., 10 ml for every gram of cells (wet weight)).

The EGTA is to help inhibit proteases that have a Ca++ cofactor. Addition of PMSF (phenyl methyl-sulfonylfluoride) and other protease inhibitors can be tried on a case to case basis. β-mercaptoethanol is included to prevent interchain disulfide bond formation upon lysis (disulfide bonds usually do not form intracellularly in *E. coli*) if the protein sensitive to EGTA, 0.5M NaCl or mercaptoethanol, adjust the buffer accordingly.

Pour the cross-linked amylose resin into an Erlenmeyer flask and let it settle. Wash the resin in at least an equal volume of column buffer+0.25% Tween-20 a few times; column buffer=10 mM sodium phosphate, 0.5M NaCl, pH 7.0 (optional: 10 mM β-mercaptoethanol, 1 mM EGTA). Pour a column of about 40–200 ml resin for each liter of culture and wash the column with 3 column volumes the same buffer. (The amount of resin depends on the resin and the amount of hybrid protein produced. "Homemade" resin binds at about 0.5 to 1 mg/ml bed volume, so for a yield of 40 mg/l you need an 80 ml column. Because the flow properties of the homemade resin are poor, a short fat column works best. Column shape is less important for this resin since it is in the form of beads; column height to diameter ratios of 4 perform well.)

Dilute the crude extract 1:5 with column buffer+0.25% Tween-20. Load the diluted crude extract at a flow rate of [10× (diameter of column in cm)$^2$]ml/hr. This is about 1 ml/min for a 2.5 cm column. The dilution of the crude extract is aimed at reducing the protein concentration to about 2.5 mg/ml. A good rule of thumb is that 1 g wet weight of cells gives about 120 mg protein.

The crude extract can be passed through the column twice to be sure that all the MBP-fusion protein is bound to the column, but in most cases all the MBP-fusion protein that is competent to bind does so on the first pass. Fusion protein can also be loaded on the resin batch-wise, by incubating crude extract and resin at 4° C. for 2–76 h with gentle agitation. Wash with 3 column volumes column buffer +0.25% Tween-20 then wash with 5 column volumes column buffer without Tween-20. Elute the hybrid protein with 10 mM sodium phosphate, 0.5M NaCl, 10 mM maltose, pH 7.0 (optional: 10 mM β-mercaptoethanol, 1 mM EGTA). Collect 10–20 fractions each=to $\frac{1}{5}^{th}$ to $\frac{1}{10}^{th}$ the column volume and assay the fractions for protein, e.g., by the Bradford assay or $A_{280}$; the fractions containing the MBP-fusion protein should have easily detectable protein. The hybrid protein elutes directly after the void volume of the column. Pool the protein-containing fractions. (Optional) Dialyze vs. 4×100 volumes 10 mM Tris-Cl, 100 mM NaCl, (optional: 1 mM EGTA) pH 8.0 to remove maltose. Concentrate in an Amicon Centricon or Centriprep concentrator, an Amicon stirred-cell concentrator, or the equivalent.

If the MBP domain is separated from the target peptide by cleavage with $FX_a$ and amylose affinity chromatography, dialyze to get rid of the maltose in your hybrid protein. In this situation, the rate at which ligand dialyzes away is inversely proportional to the concentration of the binding protein (Silhavy et al, 1975). Therefore, it is best to dialyze at a fusion protein concentration of 200 μg/ml or less, and then concentrate the fusion afterwards.

D. Preparation of Fn Fragment 1410–1516

The fibronectin fragment corresponding to Fn residues 1410–1516 is the 11.5 kilodalton (kDa) pepsin fragment of Fn was isolated as described by Pierschbacher et al, *Cell*, 26:259–267 (1981), except that the products from the pepsin digest were separated by gel filtration chromatography using Sephadex G-75-120 (Sigma, St. Louis, Mo.).

Human fibronectin was purified from human plasma as previously described herein.

6. Inhibition of Fn/Fg:GPIIb-IIIa Interaction by Fusion Protein

The ability of a fusion protein or polypeptide of the present invention to inhibit the binding interaction between GPIIb-IIIa and either fibronectin or fibrinogen was measured by competition binding to immobilized GPIIb-IIIa.

96-well Immulon-2 microtiter plates (Dynatech-Immulon) were coated with 50 μl of RGD-affinity purified GPIIb-IIIa, prepared in Example 1, diluted to 10 μg/ml in 10 mM Hepes, 0.15M NaCl, 1 mM CaCl$_2$, 1 mM MgCl$_2$.

Incubate the GPIIb-IIIa in the plate for 16 hours at 4° C., then the unbound material is removed from the wells which are then blocked with 150 μl of 5% BSA in the same buffer for 1 hour at room temperature. Wash the wells three times with 150 μl of Tyrode's buffer with 5 mM HEPES, 1 mM MgCl$_2$, 1 mg/ml dextrose, 1 mg/ml BSA. Add 50 μl of $^{125}$I Fn (125 mg/ml) at varied concentration ($4\times10^{-7}$ to $1\times10^{-10}$M) and in the presence or absence of competing reagent, such as a Fn fragment of the present invention. Incubate 4 hours to overnight at room temperature (with lead shield).

Carefully remove radioactive samples and wash 3 times with 150 μl Tyrodes with 5 mM HEPES, 1 mMMgCl$_2$, 1 mg/ml dextrose, 1 mg/ml BSA. Count with a Gamma Counter and elute by boiling in SDS-PAGE loading Buffer.

In an alternative embodiment, non-radioactive Fn may be used instead of radioactive, and detected by reacting with an appropriate anti-Fn antibody and HRP-conjugated secondary antibody. Using this variation, each antibody is incubated with the washed plate for 1 hr. The anti-Fn antibody is titrated, but a 1:1000 dilution of HRP-conjugated antibody from most manufacturers works fine. The advantage of using radioactive Fn is that the number of bound Fn molecules may determined based on the specific activity. If the amount of GPIIb-IIIa that adheres to the plastic is quantitated as well, then the stoichiometry of the binding can be determined.

In a related assay, fibrinogen (Fg) binding to GPIIb-IIIa, and inhibition thereof, is measured as above except using labelled Fg in place of Fn.

Human Fg was purified by the glycine precipitation procedure described by Kazal et al., *Proc. Soc. Exp. Biol. Med.*, 113:989–994 (1963) from fresh-frozen plasma that was treated with 10 units/ml heparin immediately after thawing. Following the final glycine precipitation, Fg was dialyzed against 50 mM Tris-HCl, 100 mM NaCl, 0.02% NaN$_3$ at pH 7.4 and stored at −80° C. until used.

7. Regeneration of Fn Polypeptides from Fusion Protein

Factor Xa cleavage of fusions is carried out at a w/w ratio of 1 or 2% the amount of fusion protein. Depending on the particular fusion protein, ratios of 0.1% to 5% will work as well. The reaction mixture can be incubated for 3 hours to 1 day, at room temperature or 4° C. Again depending on the particular fusion, it may be necessary to denature the fusion to render the factor Xa site accessible to cleavage. This can be accomplished by dialyzing in (or adding) guanidine hydrochloride to 6 M, then dialyzing against the factor Xa cleavage buffer.

If necessary, the fusion protein is dialyzed against 20 mM Tris-HCl, 100 mM NaCl, pH 8.0 (=factor Xa cleavage buffer) and a pilot experiment is performed with a small portion of the protein. For example, 20 μl fusion protein at 1 mg/ml is mixed with 1 μl factor Xa at 200 μg/ml.

In a separate tube, place 5 μl fusion protein with no factor Xa. Incubate the tubes at room temperature. At 2, 4, 8, and 16H, take 5 μl of the factor Xa reaction, add 5 μl 2× SDS-PAGE sample buffer and save on ice. Prepare a sample of 5 μl fusion protein=5 μl 2× sample buffer. Boil the samples for 5 minutes and run on an SDS-PAGE gel.

The pilot experiment can be scaled up exactly for the portion of the fusion protein to be cleaved. A small sample of the uncut fusion is saved as a reference and complete cleavage by SDS-PAGE is checked.

To denature the fusion protein, dialyze the fusion against 20 mM Tris-HCl, 6M guanidine hydrochloride, pH 8.0. Dialyze against 20 mM Tris-HCl, 100 mM NaCl, pH 8.0. Stepwise dialysis against this buffer containing decreasing amounts of guanidine hydrochloride can prevent precipitation of the fusion protein. Halving the guanidine concentration at each step is convenient; cases where 0.1M steps are necessary have been reported.

8. Discussion of Examples 1–7

In order to identify the sites of fibronectin that participate in interaction with the platelet integrin, GPIIb-IIIa, monoclonal anti-fibronectin antibodies were raised and screened for their ability to inhibit fibronectin binding to highly purified GPIIb-IIIa using the assay described in Example 6. Three antibodies able to inhibit such interaction are depicted in FIG. 1A along with a control monoclonal (Mab 15). In this figure the dose of antibody added is presented as the abscissa, and the percent binding of fibronectin to purified GPIIb-IIIa (fibronectin present at 50 nM) is on the ordinate.

Figure 1B:
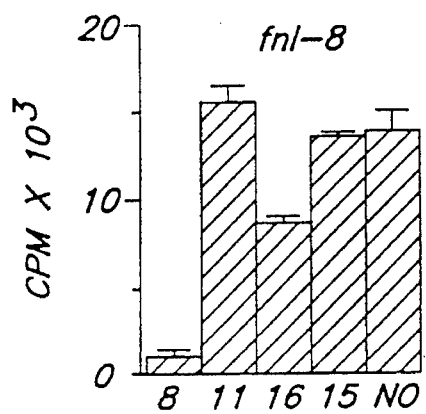
FIG. 1B, 1C and 1D are graphs that show cross competition studies of the labelled MAbs fnl-8fnl-11, and fnl-16, respectively, for sites on Fn in the presence of unlabelled MAbs. Competition is measured as an amount of MAb ($cpm \times 10^3$) binding to immobilized Fn in the presence of the indicated MAbs: Mab 8 (8), Mab 16 (16), Mab 11.10 (11), Mab 15 (15), or no Mab (NO).
Figure 1C:
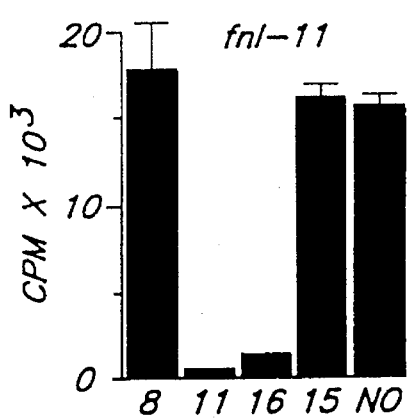
Figure 1D:
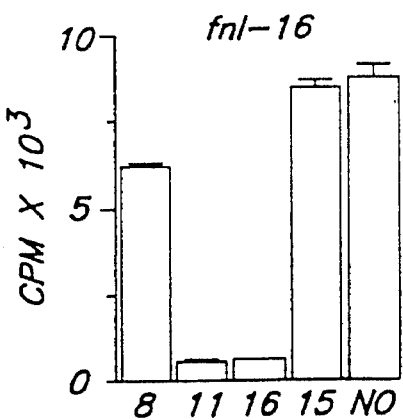

FIG. 1B, 1C and 1D show a cross-competition experiment described in Example 4 in which the radiolabelled antibodies are indicated above the bar graph and the "cold" competing antibody is indicated below the bar graph. The results indicate that MAb FnI-8 recognizes an epitope distinct from the other antibodies and that FnI-11 and 16 cross-compete with each other and therefore recognize the same epitope.

The epitopes of MAbs FnI-8, FnI-11 and FnI-16 were further characterized by measuring the ability of the MAbs to bind to regions of Fn present in various Fn fragments described herein. In that assay, direct binding was measured by placing expressed fusion protein, pepsin fragment, or cultured plasmid-containing colonies expressing a fusion protein directly onto nitrocellulose and form immobilized Fn fragments. Thereafter the nitrocellulose is contacted with a Mab as described herein for an ELISA assay to allow the MAb to bind the immobilized Fn fragments. The bound Mabs are detected using a peroxidaselabelled secondary anti-mouse antibody as previously described. The results are shown in Table 2.

TABLE 2

Mab Interactions with Fibronectin Polypeptides Encoded by cDNA Fragments

| SEQ ID NO[1] | Fibronectin[2] Residue Sequence | Mab[3] 8 | 11 | 12 | 16 |
|---|---|---|---|---|---|
| — | 934–1653 | + | + | + | + |
| (2:155–491) | 1317–1653 | + | + | + | + |
| (2:197–491) | 1359–1653 | + | + | + | + |
| (2:1–217) | 1163–1379 | − | − | − | − |
| (2:218–491) | 1380–1653 | + | − | ND | − |
| (2:248–354) | 1410–1516 | + | − | ND | − |
| (2:73–274) | 1235–1436 | + | + | + | + |
| (2:189–274) | 1351–1456 | + | + | ND | + |

[1]The SEQ ID NO and residues are indicated in the parenthesis
[2]Kornblihtt et al. EMBO J 4:1755 (1985)

TABLE 2-continued

Mab Interactions with Fibronectin Polypeptides Encoded by cDNA Fragments

| | Fibronectin[2] | | Mab[3] | | |
|---|---|---|---|---|---|
| SEQ ID NO[1] | Residue Sequence | 8 | 11 | 12 | 16 |

[3]ND = Not Determined; 8 = FnI-8; 11 = FnI-11; 12 = FnI-12; 16 = FnI-16 (IgG Kappa)

The epitopes of the anti-Fn monoclonal antibodies FnI-8, FnI-11 and FnI-16 were mapped by expressing various fragments of fibronectin in bacteria utilizing the prokaryotic expression vector lambda gt11 as described above in the form of either β-galactosidase (Bgal) or maltose binding protein (MBP) fusion proteins. In the case of fragment Fn(1410–1516), the fragment is a pepsin digest of Fn and not a fusion protein. Table 2 presents the Mab immunoreaction pattern on the various Fn fragments prepared as described in Example 5. All monoclonals reacted with a whole cDNA-expressed protein in which the RGDS sequence (residues 331–334 of SEQ ID NO 2) in the tenth type III repeat had been deleted (not shown). They also reacted with a fragment containing residues 1235–1436 which does not contain RGDS. All inhibitory antibodies also reacted with fusion proteins containing Fn fragments having Fn residues 1351–1436, 1317–1653 and 1359–1653. These data indicate that certain monoclonal antibodies against fibronectin, which inhibit its binding to GPIIb-IIIa, react with a fragment whose carboxy terminus begins at least 50 amino acids upstream of the RGDS sequence.

In addition, MAb FnI-8, and not FnI-11 or FnI-16, immunoreacted with the Fn fragments containing Fn residues 1380–1653 or 1410–1516. This latter result indicates that FnI-8 has a distinct epitope from the other two MAbs, that at a minimum includes the Fn residues 1410–1436, when one considers immunoreactivity of FnI-8 with both 1410–1516 and 1235–1436.

MAbs FnI-11 and FnI-16 each have a minimum epitope defining their immunoreactivity that includes the Fn residues 1359–1436, determined by considering at least the immunoreactivity of each MAb with both 1359–1653 and 1235–1436.

None of the inhibitory MAbs defined herein immunoreact with the Fn fragment having Fn residues 1163–1379.

To further characterize the region(s) of fibronectin that interact with GPIIb-IIIa and inhibit fibronectin binding, the construction containing bases encoding the Fn fragment 1235–1436 was expressed as a fusion protein with a maltose binding protein in a plasmid vector as described above. This fusion protein was readily purified on a crosslinked amylose column, and the capacity of this fusion protein to inhibit fibronectin binding to purified GPIIb-IIIa was assessed as described in Example 6.

Figure 3:
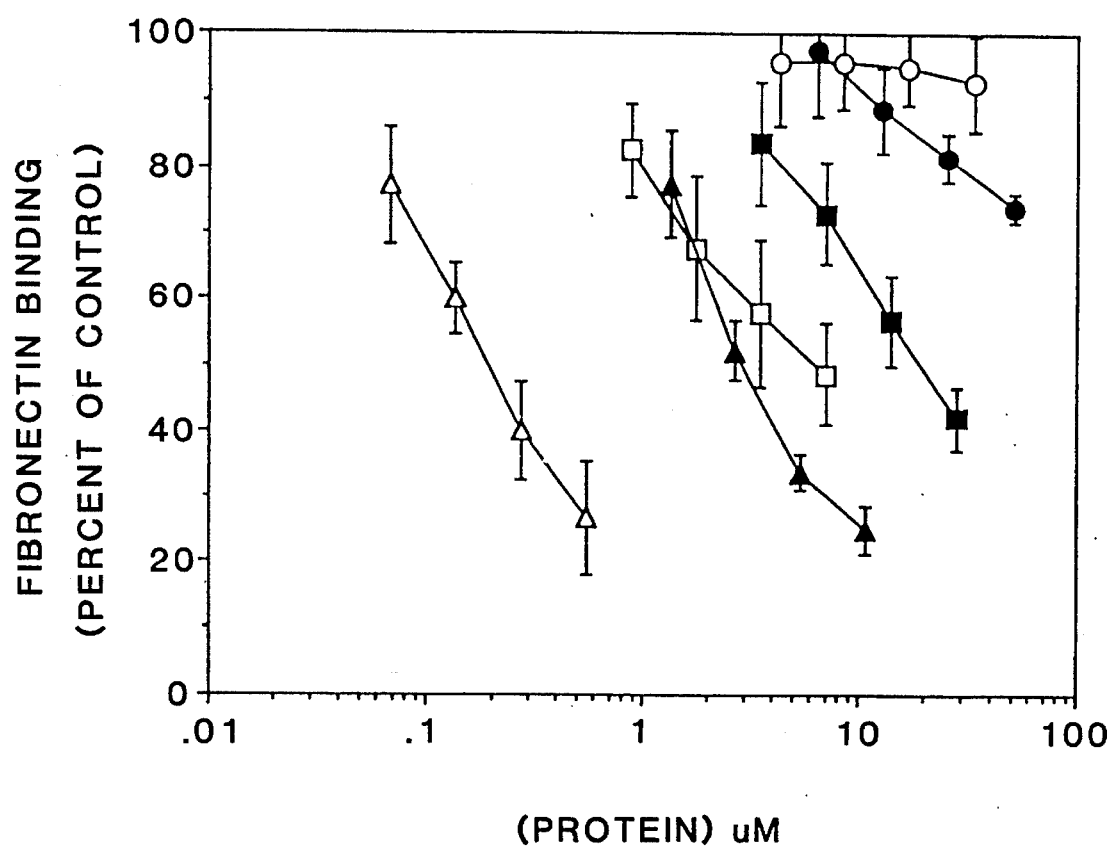
FIG. 3 shows the effect of Fn binding to immobilized GPIIb-IIIa in the presence of added inhibitory fusion proteins as described in the Examples. Fibronectin (open triangles), pepsin fragment (closed triangles), maltose-binding protein (MBP; closed circles) alone, Fn(1235–1436)-MBP fusion protein (open squares), Fn(1359–1436)-MBP fusion protein (closed squares), and control BSA alone (open circles).

In the results, shown in FIG. 3, varying concentrations of unlabelled fibronectin (open triangle), pepsin fragment, namely 1410–1516, (closed triangle), a fusion protein containing fibronectin residues 1235–1436, namely Fn(1235–1436)-MBP, (open squares), and Fn(1359–1436) (closed square) inhibited fibronectin binding to purified GPIIb-IIIa. In contrast, control bovine serum albumin (BSA; open circle) or MBP (closed circle) did not significantly inhibit Fn binding to GPIIb-IIIa. On a weight basis, the Fn(1235–1436)-MBP material was about four fold less potent than intact fibronectin, but it has numerous contaminants in addition to the insert coded polypeptide. In comparison, BSA, or the maltose binding protein alone, lacked inhibitory activity.

To further assess the nature of the inhibitor material, the mixture of fusion protein and maltose binding protein breakdown products was passed through a monoclonal FnI-16 immunoaffinity column and eluted at low pH +6M urea. The starting, pass through, and bound and eluted fractions were analyzed for the capacity to inhibit fibronectin binding to GPIIb-IIIa, and analyzed by SDS-PAGE Coommassie blue staining, and western blotted with monoclonal antibody FnI-16. Passage of the fusion protein mixture over the anti-fibronectin monoclonal antibody column resulted in quantitative removal of inhibitory activity which could be partially recovered in the low pH+Urea eluate. In contrast, passage through an irrelevant monoclonal antibody had no such effect. Inspection of the stained gels shows that the starting material was depleted of the two higher molecular weight bands by passage through the anti-fibronectin affinity column indicating that the bands are reactive with the monoclonal antibody.

To determine if the insert coded polypeptide containing fibronectin residues 1235–1436 bound GPIIb-IIIa, the capacity of microtiter wells coated with purified GPIIb-IIIa to bind the radiolabelled fusion-protein preparation was ascertained (Table 3). In addition, the radiolabelled material bound to the insolubilized GPIIb-IIIa was recovered and analyzed by SDS-PAGE followed by radioautography. The radiolabelled Fn fusion protein bound to insolubilized GPIIb-IIIa and the binding was specific and inhibited by monoclonal antibodies FnI-16 and EDTA. In contrast, there was no such binding when radiolabelled maltose binding protein alone was employed. Specific binding of fibronectin, inhibitable by the monoclonal antibody (Mab 16.12) and EDTA, was also observed (Table 3). The isolated protein products were a mixture of insert coded polypeptides containing fusion protein and maltose binding protein breakdown products. Only those bands containing the insert-coded polypeptide bound to the insolubilized GPIIb-IIIa and that binding was inhibitable by either EDTA or the monoclonal antibody FnI-16. In addition, no binding was observed to BSA coated wells. In contrast, the maltose binding protein alone failed to specifically bind to the GPIIb-IIIa coated wells.

TABLE 3

Interaction of $^{125}$I-Labelled Ligands for GPIIb-IIIa

| Ligand* | Inhibitor | Counts × 10$^{-3}$ |
|---|---|---|
| MBP/8-9 | — | 124 |
| | Mab 16.12 | 18 |
| | 2 mM EDTA | 4 |
| MBP | — | 15 |
| | Mab 16.12 | 9 |
| | 2 mM EDTA | −4 |
| Fibronectin | — | 42 |
| | Mab 16.12 | 12 |
| | 2 mM GDTA | 8 |

*MBP = Maltose binding protein
MBP/8-9 = Maltose binding protein/8-9 fusion protein The capacity of the fusion protein to inhibit fibrinogen binding to GPIIb-IIIa also was assessed. The fusion protein was observed to be an efficient inhibitor of fibrinogen binding to GPIIb-IIIa, whereas the maltose binding protein was not. The fusion protein also was observed to inhibit fibrinogen (Fg) binding to GPIIb-IIIa.

Figure 4:
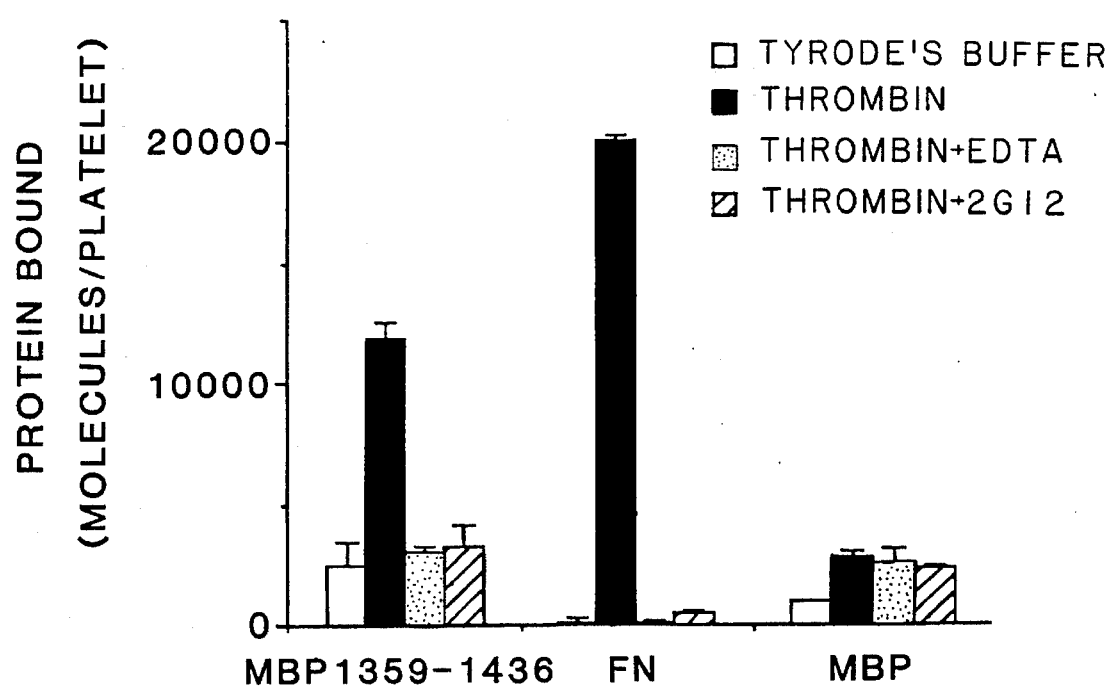
FIG. 4 illustrates direct binding of $^{125}I$ labelled Fn(1359–1436)-MBP (600 ug/ml), fibronectin (Fn:100 nM), and MBP (600 ug/ml) to resting platelets (white bars), platelets stimulated with 5 units/ml thrombin (black bars), platelets stimulated with thrombin in the presence of 5 mM EDTA (grey bars), or platelets stimulated with thrombin in the presence of 100 ug/ml MAb 2G12 (striped bars). The data is shown as the average (± one standard deviation) of triplicate measurements.

The direct binding of a Fn-derived polypeptide of this invention in the form of a fusion polypeptide was evaluated using Fn(1359–1436)-MBP in a direct binding assay with platelets using a platelet binding assay as described by Plow et al, *J. Biol. Chem.*, 256:9477–9482 (1981). Platelets that were resting, stimulated with thrombin, and with thrombin in the presence of either EDTA or a MAb that inhibits platelet stimulation, were combined with an $^{125}$I-labelled ligand, either the above fusion protein, fibronectin or control MBP. The results are shown in FIG. 4 and demonstrates that the fusion protein binds only stimulated platelets.

In sum, these data directly indicate that the insert-coded polypeptide has the capacity to bind to GPIIb-IIIa specifically, to inhibit the binding of fibrinogen and fibronectin, and thus is predicted to be an inhibitor of cell adhesive events, such as platelet aggregation. To test this hypothesis, the interaction of cells with fibronectin was examined in the presence of the fusion protein as described herein.

Thus, the fact that the insert-coded polypeptide binds directly to GPIIb-IIIa indicates that it alone, or in conjunction with an RGD sequence, could be used to promote cell attachment in clinical situations such as wound healing, prosthesis implantation, or seeding of endothelial grafts.

9. Characterization of Novel Peptide Inhibitors of Fibronectin and Fibrinogen Binding to Integrin Receptor GPIIb-IIIa As shown in Example 8, the Fn fragment in fibronectin (Fn) spanning residues 1235–1436 contained an integrin receptor GPIIb-IIIa binding site. The fragment competitively inhibited the binding to both fibronectin and fibrinogen to the receptor as shown in Example 8. To determine a minimum receptor binding region within that Fn fragment, synthetic polypeptides are generated and evaluated for their ability to bind to the receptor and competitively inhibit the binding of labelled ligand to the receptor. The approaches for characterization of a minimum receptor binding site are described below.

A. Preparation of Synthetic Polypeptides

Synthetic polypeptides of various lengths spanning the region of human Fn at residues 1235–1436 are prepared at the Scripps Clinic and Research Foundation Peptide Synthesis Core Facility (La Jolla, Calif.) using the classical solid-phase technique described by Merrifield, Adv. Enzymol., 32:221–296 (1969) as adapted for use with a model 430 automated peptide synthesizer (Applied Biosystems, Foster City, Calif.). Prepared polypeptide resins are cleaved by hydrogen fluoride, extracted and analyzed for purity by high-performance liquid chromatography (HPLC) using a reverse-phase C18 column manufactured by Waters Associates, Milford, Mass.

B. Characterization of a GPIIb-IIIa-Specific Receptor Binding Polypeptide (1) Inhibition of Fn Binding to Purified GPIIb-IIIa by a Fn-Derived Polypeptide Polypeptides synthesized in Example 9a are evaluated for their ability to competitively inhibit the binding to Fn to purified GPIIb-IIIa integrin receptor. The competition assays are performed as described by Charo et al., J. Biol. Chem., 266:1415–1421 (1991). The competition assay is performed by first admixing into individual wells of a 96 well microtiter plate (Immunlon, Dynatech) 10 µg/ml of purified GPIIb-IIIa, prepared in Example 1, diluted in HEPES-saline buffer, pH 7.4, consisting of 10 mM HEPES, 150 mM NaCl 1 mM CaCl$_2$ and 1 mMMgCl$_2$. The plates are maintained for 16 hours at 4° C. to allow the purified receptor to adsorb onto the walls of the wells. The receptor-coated wells are then washed two times with Modified Tyrode's buffer, prepared as described in Example 1, to remove any non-bound receptor from the receptor-coated wells. Non-receptor-occupied sites on the microtiter wells are blocked by admixing 5% BSA dissolved in Modified Tyrode's buffer into each well and maintaining the plate for 2 hours at room temperature.

After removing the blocking solution and washing the blocked wells as described above, 50 µl of a 10 nM solution of biotinylated Fn in Modified Tyrode's buffer is admixed into each well in the presence of polypeptides prepared in Example 9a ranging in concentration from 0.1 µM to 200 µM polypeptide to form a solid-liquid phase receptor-protein admixture. Fn admixed in the absence of polypeptides served as a positive control for the competition assay. Purified Fn is prepared as described in Example 2.

The resultant purified Fn is then biotinylated as described by Dale et al., Blood, 77:1096–1099 (1991). Briefly, for biotinylation, Fn is first dialyzed into 0.1M NaHCO$_3$ containing 0.1M NaCl at pH 8.0 and centrifuged at 100,000× g for 30 minutes at 4° C. to remove any particulate matter. The protein concentration is adjusted to 0.5 mg/ml in 50 mM sodium borate at pH 8.5. The biotinylation reaction is initiated by admixture of N-hydroxysuccinimido biotin (NHS-biotin; 0.5 mg/mg protein) (Pierce Biochemicals, Rockford, Ill.) followed by maintenance of the admixture for 2 hours at room temperature to form biotinylated Fn. The resultant biotinylated Fn is then dialyzed against Tris-HCl-saline to remove remaining salts.

The Fn-peptide admixtures are maintained in GPIIb-IIIa-coated wells for 2 hours at room temperature to allow the biotinylated Fn to bind to the receptor. Following this maintenance period, the reacted wells are washed as described above and the amount of biotinylated Fn bound to GPIIb-IIIa is determined by admixing 0.1 ml avidin bound to biotinylated horseradish peroxidase H (Hrp) (Sigma, St. Louis, Mo.) at a 1:2000 dilution to form an avidin-biotinylated Fn admixture. The admixture is maintained for 60 minutes at room temperature to allow formation of an avidin Hrp-biotinylated Fn complex. Excess avidin Hrp is removed by washing as described and the presence of biotinylated Fn bound to purified GPIIb-IIIa is detected by admixture of 50 µl of freshly prepared chromogenic substrate solution containing 4.0 mg/ml 0-phenylenediamine and 0.012% (v/v) hydrogen peroxide in CP buffer as described in Example 3a. After maintaining the color developing-reaction admixture for 10 minutes at 20° C., the reaction is stopped with the admixture of 2N H$_2$SO$_4$ and the stopped reactions are measured for absorbance as described in Example 3a.

The amount of biotinylated Fn bound to purified GPIIb-IIIa in the absence of competitor polypeptides measured at an absorbance of 490 nm yields an absorbance of 2.70..The polypeptide having the amino acid residue sequence shown in SEQ ID NO (2:248–274) which corresponds to the Fn amino acid residue sequence at residues 1410–1436, competitively inhibits the binding of Fn to purified GPIIb-IIIa. Maximal inhibition is achieved with approximately 200 µM polypeptide concentration.

A polypeptide according to the formula of SEQ ID NO (2:197–274), (2:73–274) and (2:217–274) are also prepared as in Example 9a and inhibit Fn binding to GPIIb-IIIa when tested at 200 µM polypeptide. Thus, the polypeptides defined by SEQ ID NOs (2:248–274) and (2:197–274) define two non-RGD sites on Fn of this invention that inhibit Fn or Fg binding to GPIIb-IIIa.

Although the present invention has been described in some detail by way of illustration and example for purposes of clarity and understanding, it will be obvious that certain modifications may be practiced within the scope of the appended claims.

What is claimed is:

1. A polypeptide that inhibits fibronectin binding to GPIIb-IIIa that consists of an amino acid residue sequence selected from the group consisting of the sequences shown in SEQ ID NO: 2 from residues 248–274, 197–274, 217–274 and 73–274.

2. A method for attaching cells to a substrate, which method comprises:

(a) contacting cells expressing GPIIb-IIIa on their surface with a substrate comprising a polypeptide according to claim 1 affixed to a solid-matrix; and (b) maintaining said contact for a predetermined period of time sufficient for said GPIIb-IIIa to bind said substrate, and thereby attach said cells to said substrate.

3. A method for inhibiting the binding of fibronectin or fibrinogen to platelet glycoprotein GPIIb-IIIa comprising contacting GPIIb-IIIa in an aqueous solution with an amount of a polypeptide according to claim 1 sufficient to inhibit said binding.

4. The method of claim 3 wherein said amount is from about 1 micromolar to about 1 millimolar.

* * * * *